(12) United States Patent
Ladenson et al.

(10) Patent No.: US 9,982,299 B2
(45) Date of Patent: May 29, 2018

(54) MARKERS FOR BRAIN DAMAGE

(75) Inventors: Jack Ladenson, St. Louis, MO (US); Yvonne Landt, St. Louis, MO (US); Vijay Modur, Norristown, PA (US); Omar Laterza, Jersey City, NJ (US)

(73) Assignee: Washington University, St. Louis, MO (US)

( * ) Notice: Subject to any disclaimer, the term of this patent is extended or adjusted under 35 U.S.C. 154(b) by 0 days. days.

(21) Appl. No.: 13/187,440

(22) Filed: Jul. 20, 2011

(65) Prior Publication Data

US 2012/0021534 A1     Jan. 26, 2012

Related U.S. Application Data

(63) Continuation of application No. 11/630,582, filed as application No. PCT/US2005/022606 on Jun. 27, 2005, now Pat. No. 7,985,555.

(60) Provisional application No. 60/582,998, filed on Jun. 25, 2004.

(51) Int. Cl.
*G01N 33/53*     (2006.01)
*C12Q 1/68*     (2018.01)

(52) U.S. Cl.
CPC ..... *C12Q 1/6883* (2013.01); *C12Q 2600/158* (2013.01); *G01N 33/53* (2013.01); *G01N 2800/2821* (2013.01)

(58) Field of Classification Search
CPC .... G01N 33/53; G01N 33/532–33/535; G01N 33/58–33/582; G01N 33/60; G01N 33/68; G01N 2333/47; G01N 2800/28; G01N 2800/2821; G01N 2800/2814; G01N 2800/2871
See application file for complete search history.

(56) References Cited

U.S. PATENT DOCUMENTS

2004/0018522 A1 * 1/2004 Dangond et al. ............... 435/6
2005/0260654 A1 * 11/2005 Wang ................ C12Q 1/6883
                                                  435/6.16

FOREIGN PATENT DOCUMENTS

WO    WO-01/075452     10/2001
WO    WO-04/053052     6/2004
WO    WO 2005106038 A2 * 11/2005     ........... C12Q 1/6883

OTHER PUBLICATIONS

Davidsson et al., Electrophoresis, vol. 20, 1999, pp. 431-437.*
De Vos A et al. C-terminal neurogranin is increased in cerebrospinal fluid but unchanged in plasma in Alzheimer's disease. Alzheimer's & Dementia, 2015, 11:1461-1469. (Year: 2015).*
Laterza et al., "Identification of Novel Brain Biomarkers," Clinical Chemistry (2006) 52(9):1713-1721.
Lee et al., "The Brain Injury Biomarker VLP-1 Is Increased in the Cerebrospinal Fluid of Alzheimer Disease Patients," Clinical Chemistry (2008) 54(10):1617-1623.
Notice of Reasons for Rejection (translation) for JP 2007-518337, dated Jan. 23, 2012, 5 pages.
Stejskal et al., "Determination of Serum Visinin Like Protein-1 and Its Potential for the Diagnosis of Brain Injury due to the Stroke—A Pilot Study," Biomed Pap Med Fac Univ Palacky Olomouc Czech Repub. (2011) 155(3):263-268.
Nielsen et al., "Plasma and CSF serpins in Alzheimer disease and dementia with Lewy bodies," Neurology (2007) 69:1569-1579.
Office Action for CA 2,891,635, dated Feb. 17, 2017, 6 pages.
Abbott, Nature (2003) 425:110.
Abraha et al., Ann. Clin. Biochem. (1997) 34:546-550.
Ali et al., Brit. J. Anesthesia (2000) 85:287-298.
Aurell et al., Stroke (1991) 22:1254-1258.
Barone et al., Brain Res. (1993) 623:77-82.
Baudier et al., J. Biol. Chem. (1986) 261:8192-8203.
Bernstein et al., Journal of Neurocytology (1999) 28:655-662.
Bottiger et al., Circulation (2001) 103:2694-2698.
Braunewell et al., Dementia and Geriatric Cognitive Disorders (2001) 12:110-116.
Cunningham et al., Eur. J. Clin. Invest. (1991) 21:497-500.
Dauberschmidt et al., Mol. Chem. Neuropathol. (1991) 14:237-245.
Garca-Alix et al., Acta Paediatr (2001) 90:1103-1105.
Gauss et al., Electrophoresis (1999) 20:575-600.
Hardemark et al., J. Neurosurg. (1989) 71:727-731.
Hardemark et al., Stroke (1988) 19:1140-1144.
Hata et al., "Up-Regulation of Calcineurin Aβ mRNA in the Alzheimer's Disease Brain: Assessment by cDNA Microarray", Biochemical and Biophysical Research Communications (2001) 284:310-316.
Hatfied et al., Brain Res. (1992) 577:249-252.
Hay et al., J. Neurol. Neurosurg. Psychiatry (1984) 47:724-729.
Hsieh et al., "Differential gene expression of scopolamine-treated rat hippocampus-application of cDNA microarray technology", Life Sciences (2003) 73:1007-1016.
Ilg et al., Int. J. Cancer (1996) 68:325-332.
International Search Report for PCT/US05/22606, dated Mar. 27, 2006, 4 pages.
Johnsson, Cardiothorac. Vasc. Anesth. (1996) 10:120-126.
Kato et al., Atherosclerosis (2002) 163:279-286.
Kupchak et al., Clin. Chem. (2005) 51(6):A119-A120.
Lescuyer et al., Proteomics (2004) 4:2234-2241.
Leviton et al., Acta Paediatr. (2002) 91:9-13.
Lubec et al., Progress in Neurobiol. (2003) 611:1-19.
Lynch et al., Stroke (2004) 35:57-63.
Marler et al., Science (2003) 301:167.
Mattson et al., Journal of Molecular Neuroscience (2001) 17:205-224.
Missler et al., Eur. J. Clin. Chem. Clin. Biochem. (1995) 33:743-748.
Mussack et al., Shock (2002) 18:395-400.
Nawa et al., "Elucidation of Pathological Condition in the Brain Using the Gene Expression Profile of Schizophrenia", Journal of Clinical and Experimental Medicine (2004) 208(3):133-137.
Nishi et al., Molecular Brain Research (2003) 118:102-110.
Noppe et al., Clin. Chim. Acta (1986) 155:143-150.
Persson et al., Stroke (1987) 18:911-918.

(Continued)

*Primary Examiner* — Kimberly Ballard

(74) *Attorney, Agent, or Firm* — Morrison & Foerster LLP

(57) ABSTRACT

Methods to identify markers for brain damage using fresh brain tissue and methods and compositions for detecting these markers are disclosed.

2 Claims, 26 Drawing Sheets

(56) References Cited

OTHER PUBLICATIONS

Qureshi et al., New England Journal of Medicine (2001) 344:1450-1460.
Rao, Journal of Neuroscience (2003) 71:208-219.
Reynolds, Clin. Chem. (2003) 45(10):1733-1739.
Rosand et al., Stroke (2003) 34:2512-2517.
Rothoerl et al., Acta Neurochem (2000) Suppl. 76:97-100.
Schaarschmidt et al., Stroke (1994) 25:558-565.
Schmechel et al., Science (1978) 199:313-315.
Sellman et al., Scand. J. Thor. Cardiovasc. Surg. (1992) 26:39-45.
Song et al., Journal of Neuroscience Research (2002) 68:730-737.
Spilker et al., Biochimica and Biophysics Acta (2002) 1600:118-127.
Steinberg et al., J. Neurochem. (1984) 43:19-24.
Unden, Scand. J. Infect. Dis. (2004) 36:10-13.
Vaage et al., J. Thorac. Cardiovasc. Surg. (2001) 122:853-855.
Verbeek et al., Ann. Clin. Biochem. (2003) 40:25-40.
Voet et al., Biochemistry (1990) 1102-1103.
Vos et al., Shock (2002) 18:481-482.
Warlow, Lancet (2003) 362:1211-1224.
Zimmer et al., Brain Res. Bull. (1995) 37:417-429.
Supplementary European Search Report for EP 05763857.9, dated Mar. 4, 2009, 7 pages.
Notice of Reasons for Rejection (translation) for JP 2007-518337, dated Mar. 17, 2011, 5 pages.

* cited by examiner

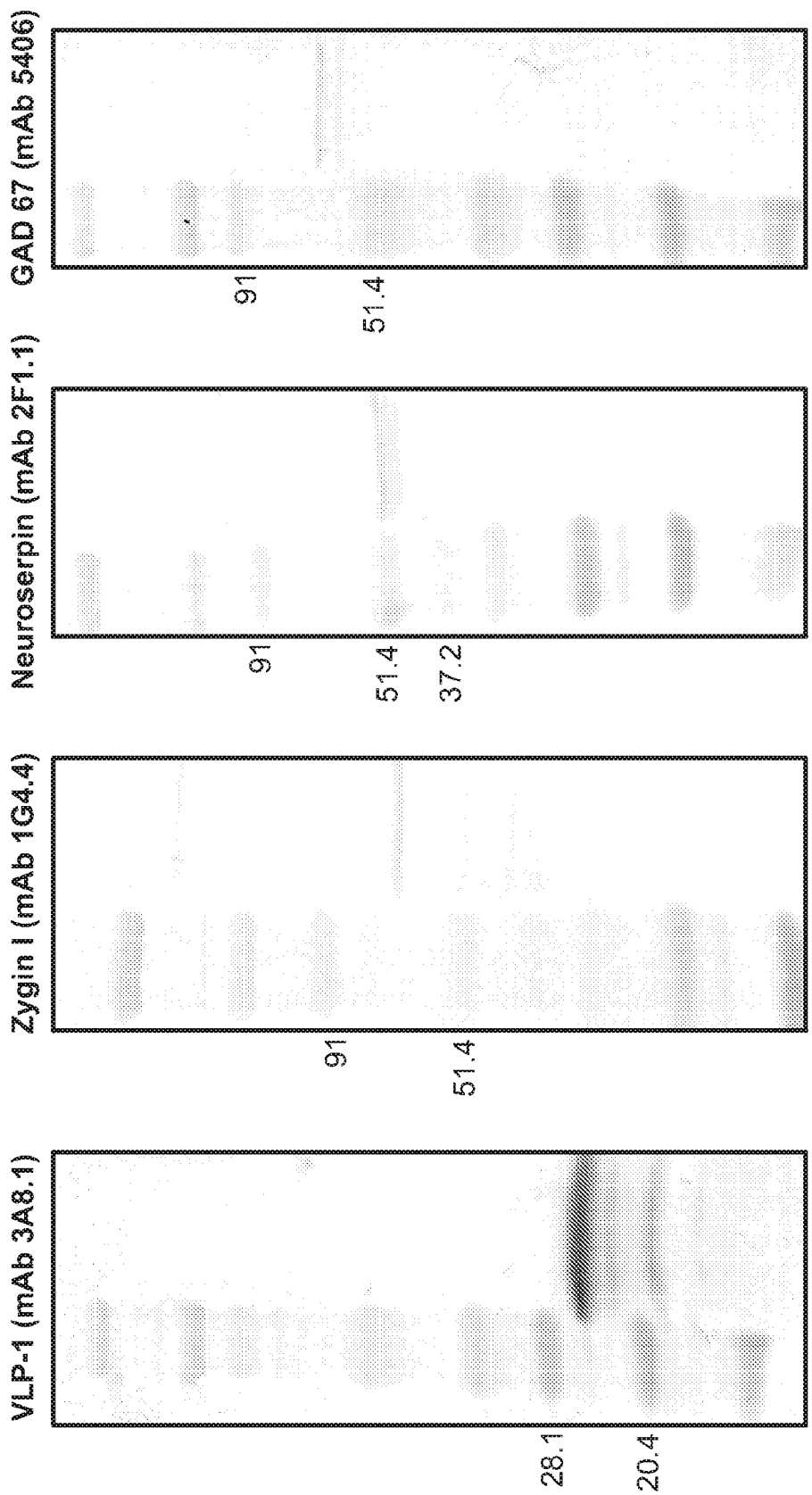

MARKERS FOR BRAIN DAMAGE

RELATED APPLICATION

This application is a continuation of U.S. Ser. No. 11/630,582, with an international filing date of 27 Jun. 2005, now U.S. Pat. No. 7,985,555, issued 26 Jul. 2011, which claims benefit under 35 U.S.C. § 119(e) to International Application No. PCT/US2005/022606, filed 27 Jun. 2005, which claims benefit of U.S. Provisional Application No. 60/582,998, filed 25 Jun. 2004. The content of each of these applications is incorporated herein by reference.

TECHNICAL FIELD

The invention relates to methods and kits to diagnose brain damage such as stroke or Alzheimer's disease in humans and corresponding conditions in other animals. More specifically, it concerns methods to identify brain damage markers, and methods to diagnose brain damage using these markers and materials for their detection.

BACKGROUND ART

Considerable effort has been exerted to identify markers that would be useful in assessing brain damage, such as that caused by stroke or Alzheimer's disease. Early diagnosis of, for example, ischemic stroke, is believed critical in order to permit an appropriate intervention, such as administration of recombinant tissue plasminogen activator which has been shown to be highly effective, if administered early, in reducing mortality and morbidity resulting from stroke. In addition, other forms of brain damage, such as hemorrhagic stroke, damage to asphyxiated term infants, brain damage resulting from cardiac surgery, Alzheimer's or miscellaneous neurodegenerative disorders are desired to be assessed; although additional diagnostic procedures may be required to distinguish among these various possibilities in some cases.

It is generally recognized that brain damage of various types can be indicated by the presence in fluids such as cerebrospinal fluid (CSF) or more conveniently, in serum or plasma or urine, of proteins or other substances that are generally characteristic of the brain. The desirability of identifying such factors that could be used for diagnoses so as to identify appropriate treatment or simply for prognosis has also been recognized widely. See, for example, Warlow, C., *Lancet* (2003) 362:1211-1224; Qureshi, A., et al., *New Eng J Med*, (2001) 344:1450-1460; Marler, J. R., et al., *Science* (2003) 301:157; Garca-Alix, A., et al., *Acta Paediatr* (2001) 90:1103-1105; Verbeek, M. M., et al., *Ann Clin Biochem*. (2003) 40:25-40.

Because of this understanding, various groups have undertaken proteomic studies of the brain to identify characteristic brain proteins. An analysis of the brain proteins in mice using 2-D electrophoresis and mass spectrometry was published by Gauss, C., et. al., *Electrophoresis* (1999) 20:575-600. The pattern showed 8,767 protein spots of which 200 were identified in the article. Two-dimensional gel electrophoresis and mass spectroscopy has been applied to CSF obtained six hours postmortem and compared to fresh CSF. Thirteen candidate proteins, some of which had been previously associated with neurodegenerative diseases were identified (Lescuyer, et al. *Proteomics* (2004) 4:2234-2241). A general analysis of this approach is described by Lubec, G., et al., *Progress in Neurobiol* (2003) 611:1-19. A news story by Abbott, A., in *Nature* (2003) 425:110 points out that while analysis of human brains has to rely on autopsied tissue, mouse brains can be analyzed at various ages using fresh tissue. Attempts have also been made to analyze genomic influences on stroke or other brain damage-associated conditions by Kato, N., et al., *Atherosclerosis* (2002) 163:279-286 and Rosand, J., et al., *Stroke* (2003) 34:2512-2517, for example.

There are a number of biomarkers of brain injury that have been reported in the scientific literature. These include S-100B, neuron-specific enolase (NSE), glial fibrillary associated protein (GFAP), myelin basic protein (MBP) and others. (Aurell, A., et al., *Stroke* (1991) 22:1254-1258; Barone, F. C., et al., *Brain Res* (1993) 623:77-82; Cunningham, R. T., et al., *Eur J Clin Invest* (1991) 21:497-500; Hardemark, H. G., et al., *J Neurosurg* (1989) 71:727-731; Hardemark, H. G., et al., *Stroke* (1988) 19:1140-1144; Hatfield, R. H., et al., *Brain Res* (1992) 577:249-252; Hay, E., et al., *J Neurol Neurosurg Psychiatry* (1984) 47:724-729; Noppe, M., et al., *Clin Chim Acta* (1986) 155:143-150; Steinberg, R., et al., *J Neurochem* (1984) 43:19-24).

S-100B is a $Ca^{2+}$-binding protein that modulates complex neuronal-glial interactions and is found mostly in glia, melanocytes, Schwann cells, Langerhans cells and anterior pituitary cells, but not in neurons. Elevated serum levels of S-100B have been associated with stroke, post-cardiac arrest brain injury and traumatic head injury. (Aurell, A, et al., *Stroke* (1991) 22:1254-1258; Hardemark, H. G., et al., *J Neurosurg* (1989) 71:727-731; Noppe, M, et al., *Clin Chim Acta* (1986) 155:143-150; Bottiger, B. W., et al., *Circulation* (2001) 103:2694-2698, Sellman, M., et al., *Scand J. Thor. Cardiovasc. Surg.* (1992) 26:39-45, Shaabam, A., et al., *Brit J Anesthesia* (2000) 85:287-298).

Leviton, A., et al., *Acta Paediatr* (2002) 91:9-13 further studied the use of S-100B, glial fibrillary acidic protein (GFAP) and NSE as markers for brain damage in children with the view to their diagnostic capability to assess such injury. Rothoerl, R. D., et al., *Acta Neurochem* (2000) Suppl. 76:97-100 showed that the serum level of S-100B is also elevated after severe head injury; Abraha, H. D., et al., *Ann Clin Biochem*. (1997) 34:546-550 suggest that measurement of serum S-100 protein is a useful prognostic marker of clinical outcome in acute stroke. Further confirmation that S-100B and NSE are significant markers of brain damage is set forth in Mussack, T., et al., *Shock* (2002) 18:395-400 and in a comment on this article by Vos, P. F. et al., *ibid*. 481-482. It is noted that increased serum concentrations of S-100B, GFAP, and NSE have been associated with various acute central nervous system disorders.

However, S-100B is not brain specific (Vaage, J., et al., *J Thorac Cardiovasc Surg* (2001) 122:853-855; Unden, J., *Scand J Infect Dis* (2004) 36:10-13) since it is also expressed in white and brown adipose tissue, skin, skeletal muscle, melanoma and glioblastoma cells (Zimmer, D. B., et al., *Brain Res Bull* (1995) 37:417-429; Ilg, E. C., et al., *Int J Cancer* (1996) 68:325-332), as well as in muscle, heart and the kidneys (Baudier, J, et al., *J Biol Chem* (1986) 261: 8192-8203; Missler, U., et al., *Eur J Clin Chem Clin Biochem* (1995) 33:743-748).

NSE represents the gamma, gamma-dimer of the protein enolase (2-phospho-D-glycerate hydrolase), which is a soluble enzyme of the glycolytic pathway with a total molecular weight of approximately 80 kDa (Schmechel, D., et al., *Science* (1978) 199:313-315). NSE is expressed in neuronal cytoplasm and dendrites and in cells of the amine precursor uptake and decarboxylation (APUD) cell system. Early clinical studies are available demonstrating elevated serum NSE titers in stroke or cardiac arrest patients (Persson, L., et al., *Stroke* (1987) 18:911-918; Dauberschmidt, R., et al., *Mol Chem Neuropathol* (1991) 14:237-245; Schaarschmidt, H, et al., *Stroke* (1994) 25:558-565. In addition, tumor cells in APUDomas, neuroblastomas, seminomas, and small-cell carcinoma of the lung also express NSE. For this reason, NSE has been studied as a diagnostic and prognostic serum marker in clinical management of such neoplasms. However, NSE can also be found in red cells and platelets and cannot be considered specific for brain (Johnsson, P. J., *Cardiothorac Vasc Anesth* (1996) 10:120-126).

Combinations of markers have been used in an attempt to obtain better sensitivity and specificity for stroke. One group has utilized the combination of brain markers neuron-specific enolase, myelin basic protein, and S-100B (Kupchak, P., et al., *Clin Chem* (2005) 51(6):A119 and A120; abstracts). Another group evaluated >50 protein biomarkers and chose S-100B, B-type neurotrophic growth factor, Von Willebrand factor, matrix metalloproteinase-9 and monocyte chemotactic protein-1 (Reynolds, M., *Clin Chem* (2003) 45(10):1733-1739). In another study, biomarkers based on brain damage (S100B), inflammation (matrix metalloproteinase-9 and vascular cell adhesion molecule) and thrombosis (Von Willebrand factor) were combined to identify acute stroke (Lynch, et al., *Stroke* (2004) 35:57-63).

An application has been submitted to FDA for a multi-marker diagnostic device for acute stroke by Biosite, Inc. The markers are S-100B, brain natriuretic protein, D-dimer, and matrix metalloproteinase-9.

At present, there is a need for additional and more reliable markers of brain damage than those currently available, even if combined with markers of phenomena other than brain injury. As noted above, all currently utilized brain damage markers are not sufficiently specific.

DISCLOSURE OF THE INVENTION

The invention provides methods to identify markers of brain damage and methods to predict the presence and progression of brain damage using these markers. Typically, the markers are proteins or their encoding mRNA's that demonstrate enhanced expression of the relevant gene in the brain. When these markers are detected in body fluids, e.g., in cerebrospinal fluid, blood, or in urine they are associated with the tissue damage characteristic of brain damage.

A particularly important form of brain damage is stroke, which affects large numbers of individuals and, if correctly identified sufficiently early, permits effective treatment. It is estimated that many stroke victims die or exhibit vastly decreased quality of life due to the inability of currently used approaches correctly to diagnose and treat the condition in sufficient time. Other indications where brain damage is significant include but are not limited to trauma, damage due to asphyxiation, damage associated with invasive surgery, and neurodegenerative diseases such as Alzheimer's.

Thus, in one aspect, the invention is directed to a method to identify markers useful in brain damage diagnosis which method comprises assessing fresh or fresh-frozen brain tissue for gene expression and comparing the levels of gene expression in said fresh or fresh-frozen brain tissue with expression levels of the same genes in other fresh or fresh-frozen tissues, such as muscle or liver. Genes with expression levels at least 10-fold higher in fresh brain than in alternative tissues are identified as generating mRNA or protein markers for brain damage. Additional criteria that can be used to identify these markers are 1) genes that show expression levels of mRNA at least 10,000 times background in brain tissue; 2) genes that encode proteins of <70 kD molecular weight; and 3) instances in which the protein encoded by the gene is detectable in the brain using Western blot or other standard techniques. Expression at high levels above background assures sufficient abundance in the brain for the expression markers to be useful as detection targets.

As further described below, it is particularly important that the method employ fresh or fresh-frozen brain tissue as could be derived from laboratory animals such as mice, rats or rabbits since the levels of mRNA and protein in brain (or other tissues) can be altered when the tissue is stored improperly, or in the case of direct testing on human brains, when the brain is in an unnatural state as would be necessarily the case in autopsied tissue. There is no detriment to utilizing this surrogate species, as human analogs of the markers determined in fresh animal tissue can readily be identified. Furthermore, antibodies, including monoclonal antibodies, are prepared that are cross-reactive with the markers identified in laboratory animals and their human counterparts.

In a second aspect, the invention is directed to a method to diagnose the occurrence of, or a high probability of subsequent occurrence of, brain damage in a subject which method comprises analyzing biological fluids of said subject for the presence of one or more markers identified as described above. In particular, these markers include, but are not limited to, the products of genes located at gene I.D. No. 7447 (VSNL1) encoding visinin-like 1 (VLP-1), gene I.D. No. 6616 (SNAP25) encoding synaptosomal-associated protein, 25 kDa, gene I.D. No. 2571 (GAD1) encoding glutamate decarboxylase 1 (brain, 67 kDa (GAD67), gene I.D. No. 4336 (MOBP) encoding myelin-associated oligodendrocyte basic protein, gene I.D. No. 6857 (SYT1) encoding synaptotagmin I, gene I.D. No. 10382 (TUBB4) encoding tubulin, beta 4, gene I.D. No. 9638 (FEZ1) encoding fasciculation and elongation protein zeta 1 (zygin I), gene I.D. No. 2743 (GLRB) encoding glycine receptor, beta, gene I.D. No. 140767 (VMP) encoding vesicular membrane protein p24, gene I.D. No. 10439 (OLFM1) encoding olfactomedin 1, gene I.D. No. 7545 (ZIC1) encoding Zic family member 1 (odd-paired homolog, *Drosophila*), gene I.D. No. 29993 (PACSIN1) encoding protein kinase C and casein kinase substrate in neurons 1, gene I.D. No. 5354 (PLP1) encoding Proteolipid protein 1 (Pelizaeus-Merzbacher disease, spastic paraplegia 2), gene I.D. No. 9118 (INA) encoding internexin neuronal intermediate filament protein, alpha, gene I.D. No. 140679 (SLC32A1) encoding solute carrier family 32 (GABA vesicular transporter), member 1, gene I.D. No. 5274 (SERPINI1) encoding serine (or cysteine) proteinase inhibitor, clade I (neuroserpin), member 1, gene I.D. No. 4826 (NNAT) encoding Neuronatin, gene I.D. No. 2566 (GABRG2) encoding gamma-aminobutyric acid (GABA) A receptor, gamma 2, gene I.D. No. 6844 (VAMP2) encoding vesicle-associated membrane protein 2 (synaptobrevin 2), or gene I.D. No. 4900 (NRGN) encoding neurogranin (protein kinase C substrate, RC3).

The foregoing have been identified as expressed at sufficiently high levels specifically in fresh brain using the method of the invention, which is characterized by employing fresh brain tissue, as illustrated using murine subjects.

In another aspect, the invention is directed to compositions useful in determining the presence or levels of the markers of the invention in biological fluids of subjects to be diagnosed. Such compositions or reagents include antibodies specifically immunoreactive with the proteins encoded by the relevant genes, oligonucleotide probes specifically hybridizing under stringent conditions to the mRNA transcribed from these genes, and oligonucleotide primers appropriate to amplify said mRNA.

Also included within the scope of the invention are kits for diagnosis which contain antibodies, oligonucleotide probes, and/or primers and other reagents for identifying association of these reagents with targets in the biological fluid samples.

BRIEF DESCRIPTION OF THE DRAWINGS

FIGS. 2A-D show the results of Western blot of brain tissue homogenate demonstrating the presence of the protein expression products of genes VSNL-1, FEZ1, SERPINI1 and GAD1.

MODES OF CARRYING OUT THE INVENTION

Figure 1A:
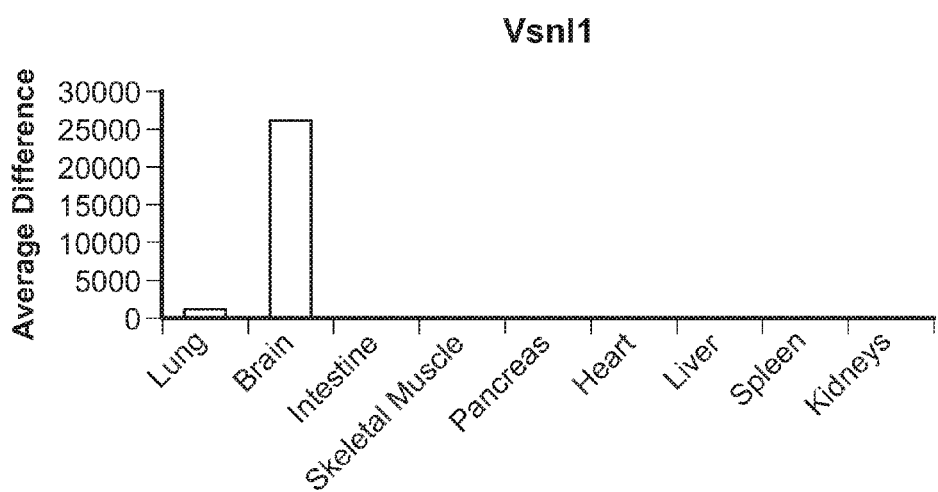
FIGS. 1A-1T show the comparative mRNA levels of 20 brain damage markers in brain and other tissues.

By using fresh brain tissue, as opposed to preserved brains or autopsied brains, applicants have succeeded in identifying a number of genes which are expressed at much higher levels in the fresh brain tissue than are expressed in non-brain tissues such as lung, intestine, skeletal muscle, pancreas, heart, liver, spleen, or kidney. Fresh brain tissue can be obtained from experimental laboratory animals, such as rabbits, rats, mice, guinea pigs, and the like. (As used herein, "fresh" includes fresh frozen.) A preferred source is fresh brain tissue from mice. The non-brain tissue used for comparison is preferably fresh as well and obtained from the same subject. In the examples below, expression is detected by utilizing gene microarrays; other methods of assessing expression are also applicable, including quantitative RT-PCR, immunoassays for protein, and the like. Methods to assess gene expression are well known in the art and many such methods are commercially available.

As set forth above, a number of genomic loci have been identified as highly expressed in brain, but at much lower levels, or not at all in other tissues and organs. Transit of the expression products of these loci from the brain itself into biological fluids is verified as associated with brain damage or the probability of, for example, stroke onset. In addition, antibodies have been prepared that are specifically immunoreactive with some of the proteins identified. These antibodies, as well as other specific binding partners, are useful in methods for stroke diagnosis by detecting proteins in biological fluids.

A primary criterion for identifying a gene as generating an mRNA or protein marker for brain damage is specificity of expression in the brain. In particular, genes were chosen whose mRNA expression levels in brain were at least 10 times higher than expression levels in a variety of other tissues including lung, intestine, skeletal muscle, pancreas, heart, liver, spleen and kidneys. Additional criteria are also helpful. It is useful to assure an expression level in the brain that will provide sufficient target for detection in the assay. This criterion is referred to as the level of expression as compared to background. When mRNA levels are employed as the criterion, the background is defined as signals obtained from mismatch oligonucleotides in a GeneChip® array format. That is, the average difference values for the mRNA generated by the gene in question are the difference between the signal intensity of the appropriate RNA (generated when a perfect match occurs) and the signal created when mismatch oligonucleotides are employed. Details of this criterion are set forth in Example 1. Genes that give mRNA expression with levels more than 10.000-fold above said background are considered sufficiently abundant in the brain to provide a basis for detection.

Further, if assays are to be conducted at the protein level, it is desirable to assure the presence of adequate levels of proteins by assaying brain tissue homogenates using Western blot. Most of the genes identified as markers in the present application provide detectable levels of protein from brain homogenates on Western blot. Further, if assays at the protein level are employed, it is desirable to select genes that encode proteins of <70 kDa to assure ability to pass through the blood-brain bather.

The first two criteria (10-fold higher expression in the brain as compared to other tissues) and a 10,000-fold higher level of expression versus background are particularly significant when mRNA is used as a marker, and the appearance of protein on Western blot and selection of proteins of <70 kDa are particularly important when protein is used as the marker.

Biological fluids that are useful as samples for the detection methods of the invention include blood and fractions thereof, such as plasma or serum, cerebrospinal fluid, urine, and lymphatic fluids, Serum or plasma or urine are more convenient. The subjects may be human patients, or may be animals such as domesticated companion animals, farm animals, experimental laboratory animals, or any vertebrate system subject to brain damage. Thus, the subjects may be humans, cows, horses, pigs, cats, dogs, rats, rabbits, mice, chickens and other fowl, or horses. Of greatest interest is detection of these markers in biological fluids of humans.

A wide variety of methods to detect gene expression in biological fluids is available. A very brief exemplary list would include detection of mRNA levels using quantitative PCR with oligonucleotide primers as reagents, Northern blot or other formats using oligonucleotide probes that hybridize specifically to mRNA transcribed from the loci as reagents, immunoassays using antibodies to detect the levels of the encoded protein and a multiplicity of other methods dependent, for example, on other indicators of protein or mRNA levels, such as mass spectral patterns and chromatographic methods. The skilled practitioner will be aware of these and many other methods to detect expression levels.

In more detail with regard to one exemplary method of the invention. immunoassays are a convenient embodiment. For use in such assays, antibodies specifically immunoreactive with the marker protein can be prepared by known procedures involving immunization of suitable subjects, such as mice, rabbits, or goats and preparation of polyclonal serum or, preferably, preparation of monoclonal forms of the antibodies using spleen or other sources of B-cells and standard fusion techniques. In addition, genes encoding monoclonal antibodies may be isolated and used to produce recombinant forms, including modified forms such as Fv single-chain antibodies. Fragments of antibodies which are themselves immunoreactive with the target proteins can also be used in the assays. As the antibodies are used in in vitro diagnosis, there may be no reason to further modify, for example, murine antibodies to prepare human/murine chimeras or to humanize them for human diagnosis. However, use of such modified forms is not excluded.

As used herein, "antibodies" includes the various forms of immunoglobulins and immunoreactive fragments of these proteins. For example, "antibodies" includes, but is not limited to, polyclonal antibodies, monoclonal antibodies, fragments such as Fab, Fab', F(ab')$_2$, single-chain antibodies (Fv), chimeric antibodies, antibodies recombinantly produced or antibodies produced from hybridomas, and the like. Humanized antibodies are also included, though their use in in vitro diagnosis is not required.

Disclosed hereinbelow are specific monoclonal antibodies or polyclonal antibodies useful in detecting some of the marker proteins of the present invention. These antibodies recognize specific epitopes of the protein specifically bound by them. The invention is also directed to these antibodies and to antibodies which bind the same epitopes as do these exemplified antibodies. By indicating that an antibody is 'immunoreactive' with a particular protein is meant that the antibody (or immunoreactive fragment) binds to that protein in a manner that permits its detection in a complex environment. It is understood that many antibodies are crossreactive with other proteins, but generally at levels much less than those with which they are specifically immunoreactive.

Immunoassays may be performed in many formats including direct and competitive sandwich assays, assays which utilize radioactive tracers as detection reagents, fluorescence detection, chemiluminescent detection, detection by complexation with enzymes (ELISA assays) or various forms of flow cytometry. Such approaches will be well known to the practitioner. A particular embodiment exemplified herein employs monoclonal antibodies in a sandwich assay and detection with labeled capping antibody. The labeled capping antibody described is a purified rabbit polyclonal antibody but could be a mono or polyclonal antibody from a variety of sources. A variety of other protocols could also be used, such as lateral flow assays, centrifugal flow assays, assay strips, homogeneous assays and the like.

In another aspect, the invention includes kits useful for performing diagnosis. If the assay is an immunoassay, the kit will include at least an antibody or fragment or modified form thereof which is immunoreactive with the designated marker. It may also include additional antibodies for detection of the resulting complex or other reagents for such detection. The assay kit may also include solid support for capture and labeling of the analyte.

Kits which depend on detection of mRNA will include specific primers designed to amplify the mRNA encoding the marker or an oligonucleotide probe which will hybridize thereto. Suitable detection reagents are also included.

In either case, any specific binding partner for the analyte expression product may be used—e.g., a ligand for receptor protein and vice versa, or reagents specifically designed to bind target RNA or DNA generated therefrom may be employed.

The following examples are offered to illustrate but not to limit the invention.

EXAMPLE 1

Identification of Genes Overexpressed in Brain

Brain, liver, spleen, kidney, skeletal muscle, lung, pancreas, heart and small intestine from three (two male and one female) C57BL/6 mice (Jackson labs) of age 4-6 weeks were obtained by careful dissection. The organ samples were snap frozen in liquid nitrogen and processed to isolate RNA. Quality of the RNA was confirmed by: 1) spectrophotometry of RNA with an absorbance at 260 nm/A280 nm-ratio>1.9; 2) the 28S/18S ratio of extracted RNA was >1.4 as observed by RNA LabChip (Agilent 2100 Bioanalyzer RNA 6000 LabChip kit).

From the total RNA, biotinylated cRNA probes were generated, fragmented and applied to Mouse MU74A (Version 1) GeneChip® arrays (Affymetrix, Santa Clara, Calif.). The overall fluorescence intensity across each chip was scaled to 1500 with Affymetrix analysis software, Microarray Suite. The data were transferred to Microsoft Excel work sheet. One selection criterion was gene expression with average difference values>10,000 in the brain (i.e., signal intensity of each mRNA computed by Affymetrix software that calculates the difference between the perfect match and mismatch oligonucleotides which are part of the gene chip array). The average difference values as described above reflect an expression level above "background" and demonstrate sufficient abundance of the expression products to provide a suitable marker. An average difference value of 10,000 was chosen because this suggests a high degree of abundance of the transcripts in the brain. The second criterion was expression in the brain greater by ten-fold versus spleen, kidney, skeletal muscle, lung, pancreas, heart and small intestine. Twenty-nine genes met these criteria and were selected.

The human homologs of this list of genes were perused in the bioinformatics databases Entrez Gene found at ncbi.nlm.nih.gov/entrez/query.fcgi?db=gene;

OMIM found at ncbi.nlm.nih.gov/entrez/query.fcgi?db=OMIM; and

Unigene found at ncbi.nlm.nih.gov/entrez/query.fcgi?db=unigene.

By this analysis, we found that 26 of the 29 had human homologs that were confirmed to be enriched in the brain in humans by the abundance of Expressed Sequence Tags (EST's) derived from a brain source in Unigene.

Two of the gene products, myelin basic protein and neuron-specific enolase have been tested previously as brain injury markers and were excluded from this list.

Of the 24 remaining gene products on the list, only 20 of the human homologs have predicted protein sequence chain length of less than 70 kDa.

These gene products with predicted protein sequence chain length of less than 70 kDa were designated as candidate brain-injury markers. The 70 kDa cut-off was selected because albumin, a protein abundant in the plasma, is known to enter the brain after injury due to damage to the blood brain barrier (Cornford, E. M, et al., *Adv Drug Deliv Rev* (1999) 5; 36(2-3):145-163; Hampel, H, et al., *Alzheimer Dis Assoc Disord* (1997) 11(2):78-87; Gingrich, M. B, et al., *Trends Neurosci* (2000) 23(9):399-407 suggesting that this cut-off value for the egress of proteins from the brain would also be similar.

Thus, from this analysis, 20 brain-specific candidates were selected. The human homologs of these candidate genes are shown by their gene identifiers in Table 1 in order of their mRNA expression in mouse brain.

TABLE 1

Human Genes identified as brain-specific markers

| Gene Symbol | Gene Product Name | Entrez Gene ID | Unigene Cluster |
|---|---|---|---|
| VSNL1 | visinin-like 1 (VLP-1) | 7447 | Hs.444212 |
| SNAP25 | synaptosomal-associated protein, 25 kDa | 6616 | Hs.167317 |
| GAD1 | glutamate decarboxylase 1 (brain, 67 kDa) | 2571 | Hs.420036 |
| MOBP | myelin-associated oligodendrocyte basic protein | 4336 | Hs.121333 |
| SYT1 | synaptotagmin I | 6857 | Hs.310545 |
| TUBB4 | tubulin, beta 4 | 10382 | Hs.110837 |
| FEZ1 | fasciculation and elongation protein zeta 1 (zygin I) | 9638 | Hs.224008 |
| GLRB | glycine receptor, beta | 2743 | Hs.32973 |
| VMP | vesicular membrane protein p24 | 140767 | Hs.49230 |
| OLFM1 | olfactomedin 1 | 10439 | Hs.522484 |
| ZIC1 | Zic family member 1 (odd-paired homolog, Drosophila) | 7545 | Hs.41154 |
| PACSIN1 | protein kinase C and casein kinase substrate in neurons 1 | 29993 | Hs.520087 |
| PLP1 | Proteolipid protein 1 (Pelizaeus-Merzbacher disease, spastic paraplegia 2) | 5354 | Hs.1787 |
| INA | internexin neuronal intermediate filament protein, alpha | 9118 | Hs.500916 |
| SLC32A1 | solute carrier family 32 (GABA vesicular transporter), member 1 | 140679 | Hs.179080 |
| SERPINI1 | serine (or cysteine) proteinase inhibitor, clade I (neuroserpin), member 1 | 5274 | Hs.478153 |
| NNAT | Neuronatin | 4826 | Hs.504703 |
| GABRG2 | gamma-aminobutyric acid (GABA) A receptor, gamma 2 | 2566 | Hs.7195 |
| VAMP2 | vesicle-associated membrane protein 2 (synaptobrevin 2) | 6844 | Hs.25348 |
| NRGN | neurogranin (protein kinase C substrate, RC3) | 4900 | Hs.524116 |

The mRNA/protein products of the foregoing genes are thus predicted to be present in cerebrospinal fluid, blood or urine after brain injury or more generally as an indicator of brain damage.

Figure 1B:
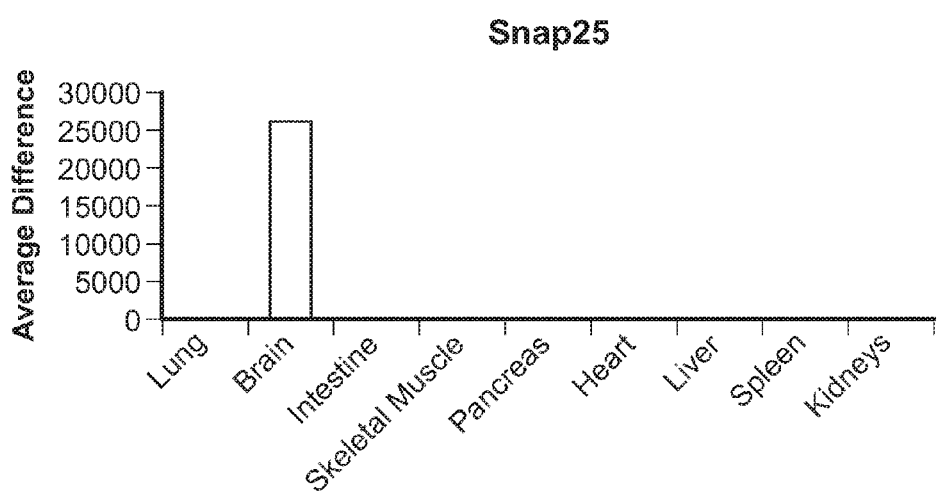
Figure 1C:
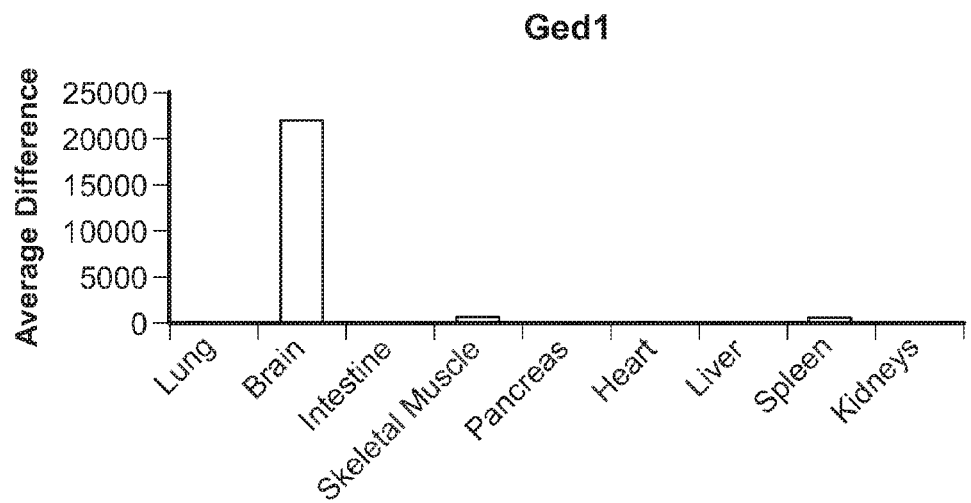
Figure 1D:
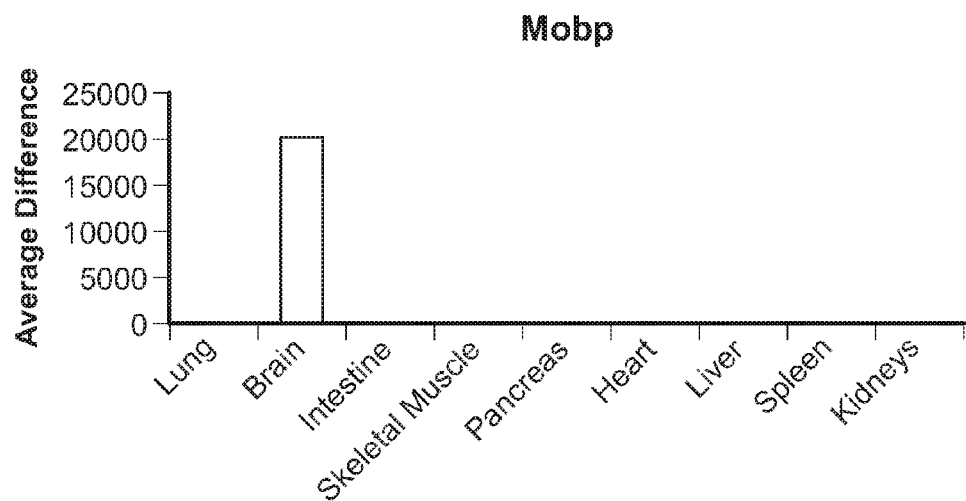
Figure 1E:
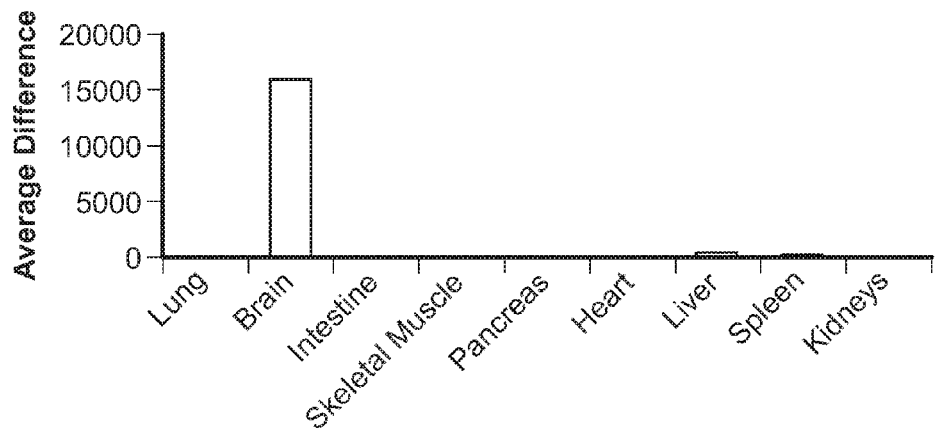
Figure 1F:
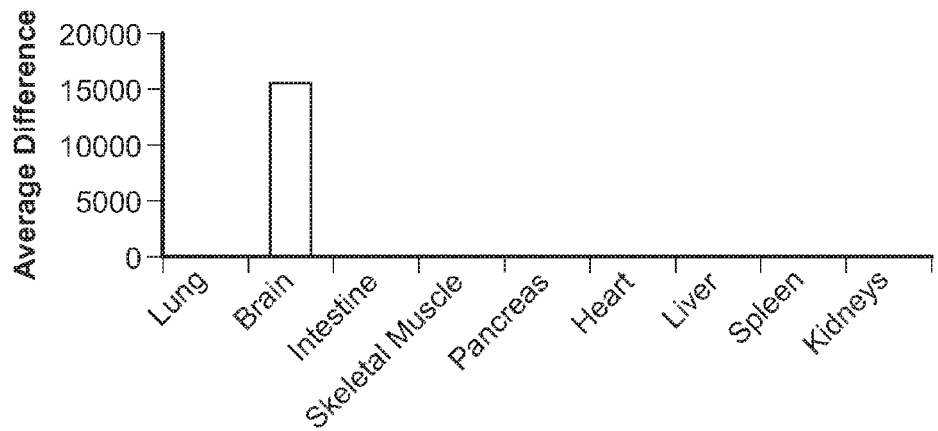
Figure 1G:
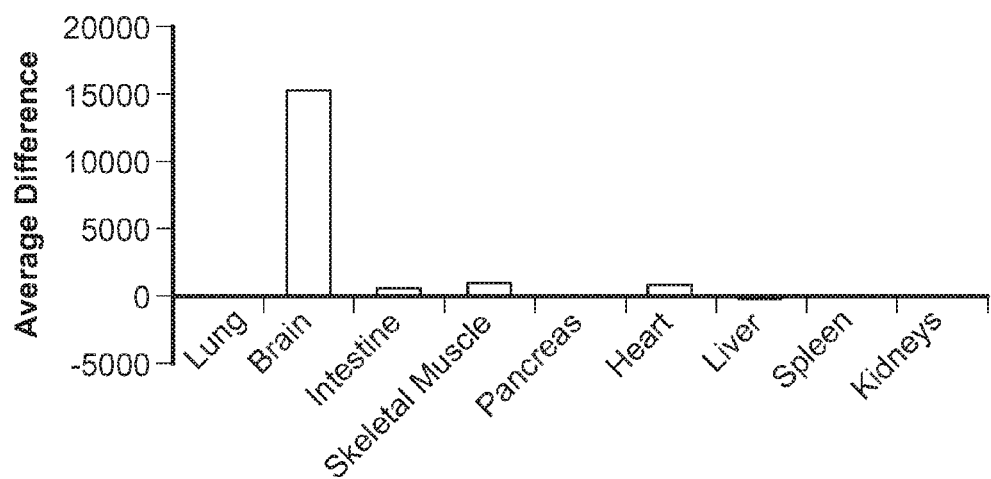
Figure 1H:
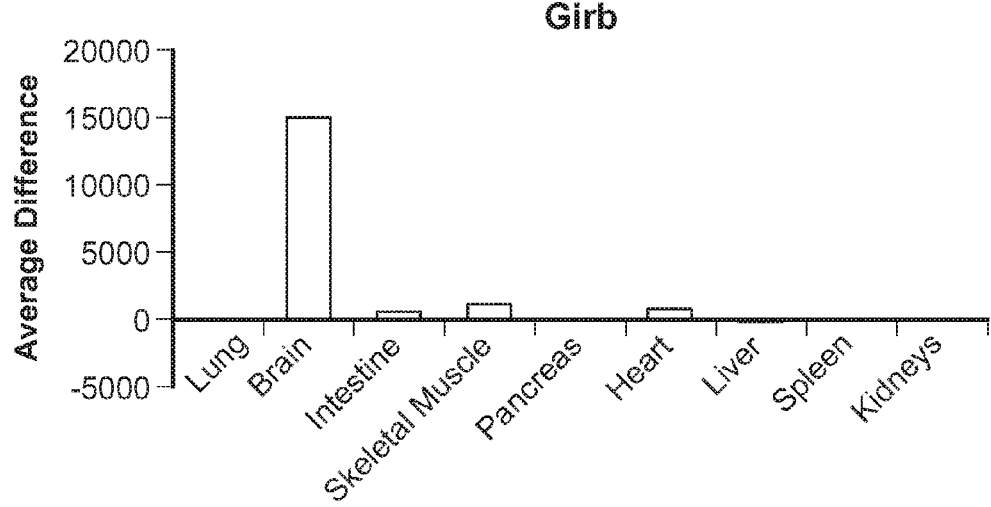
Figure 1I:
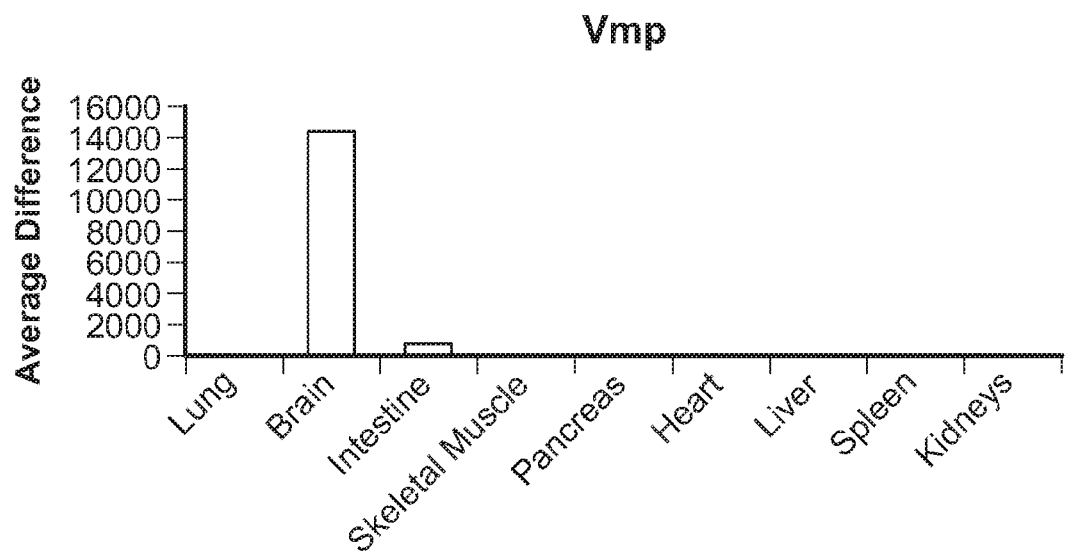
Figure 1J:
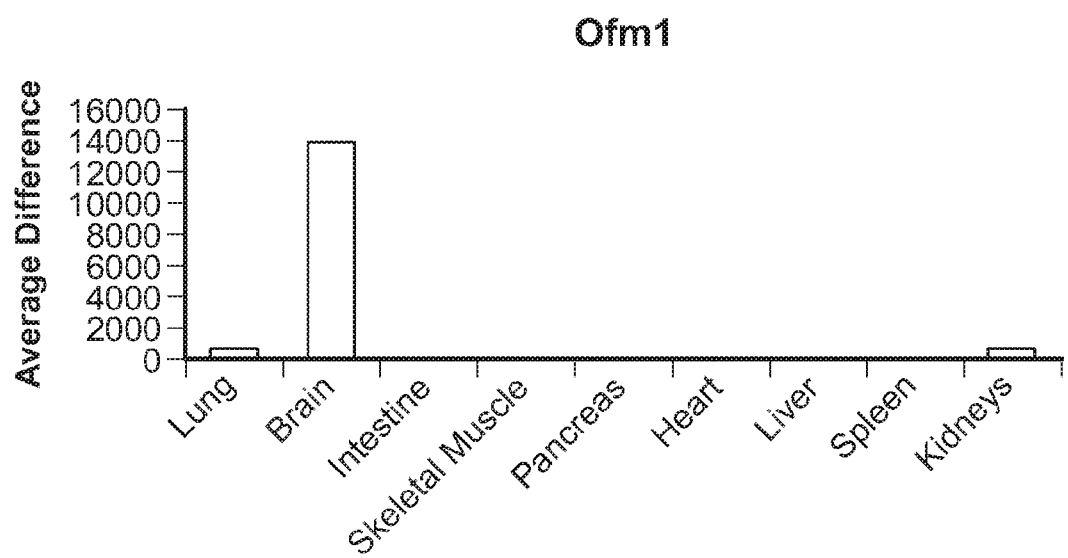
Figure 1K:
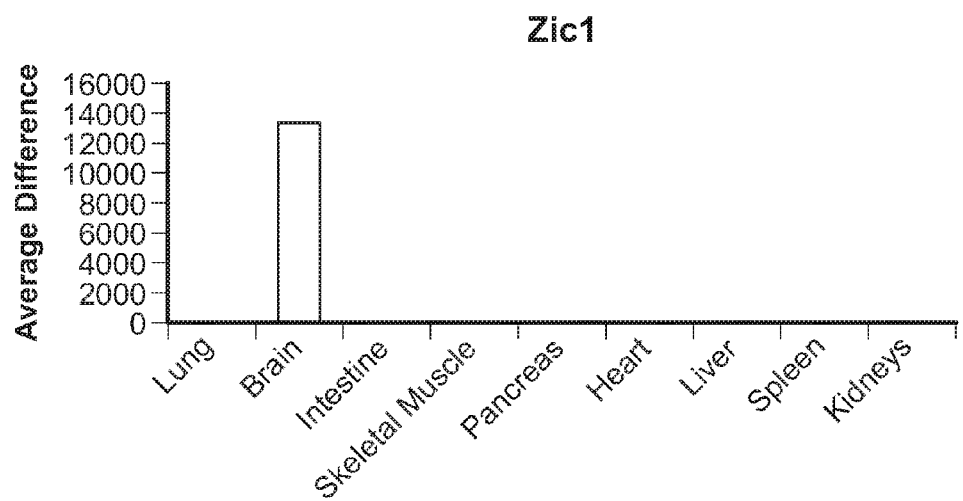
Figure 1L:
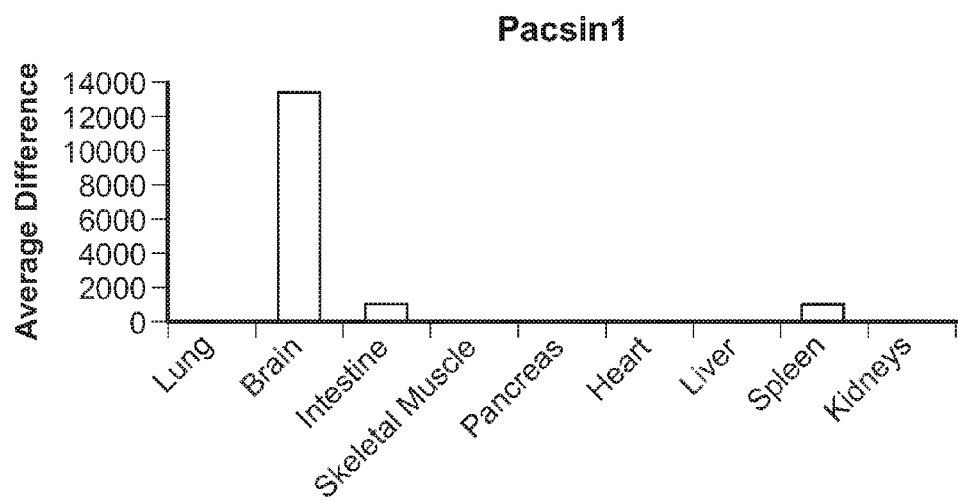
Figure 1M:
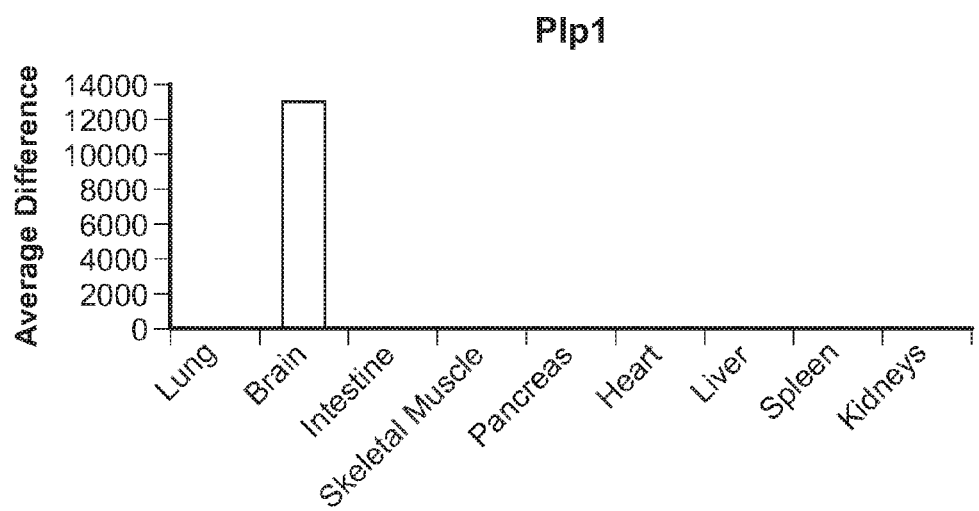
Figure 1N:
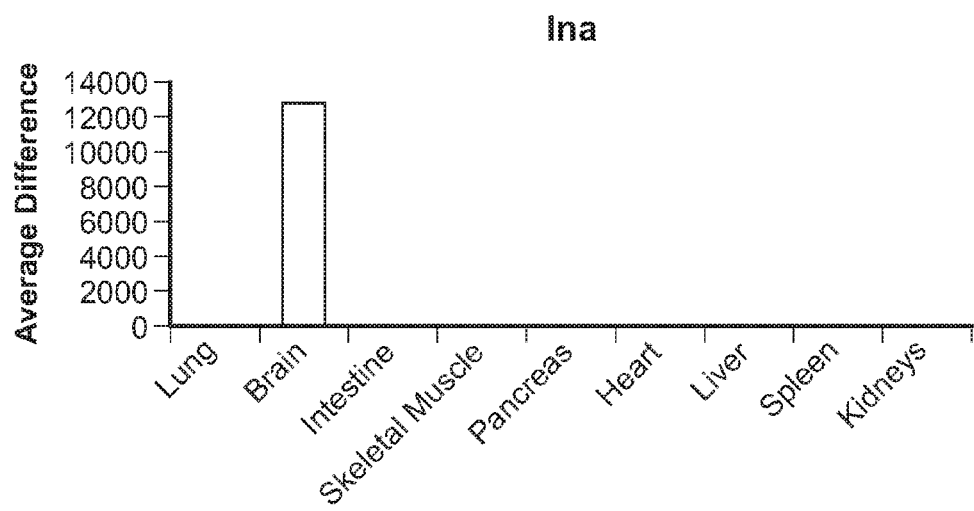
Figure 1O:
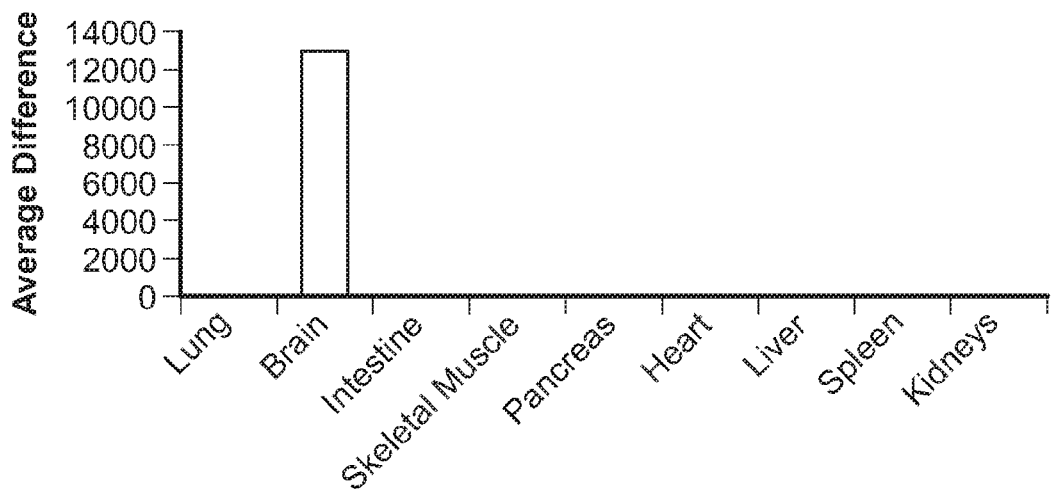
Figure 1P:
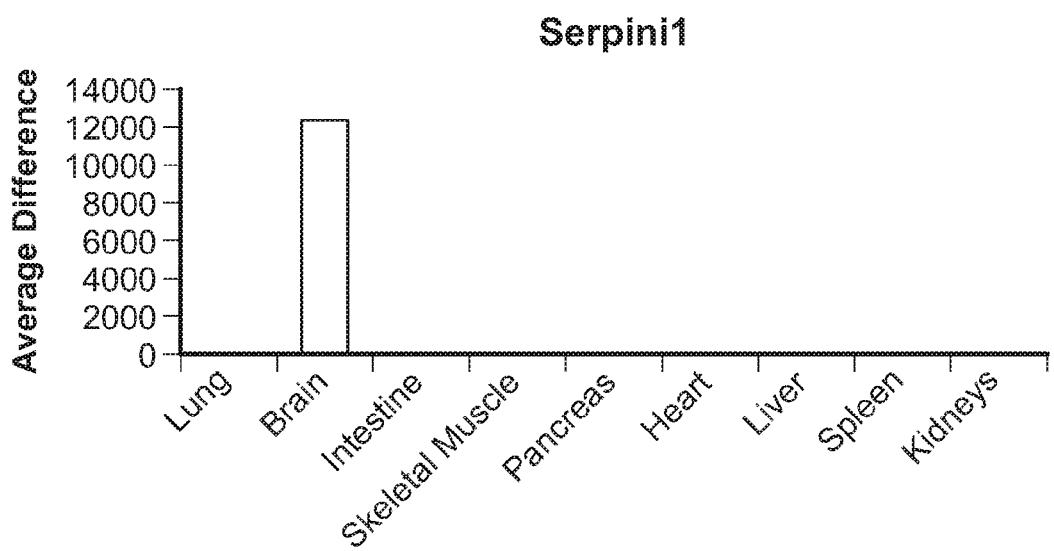
Figure 1Q:
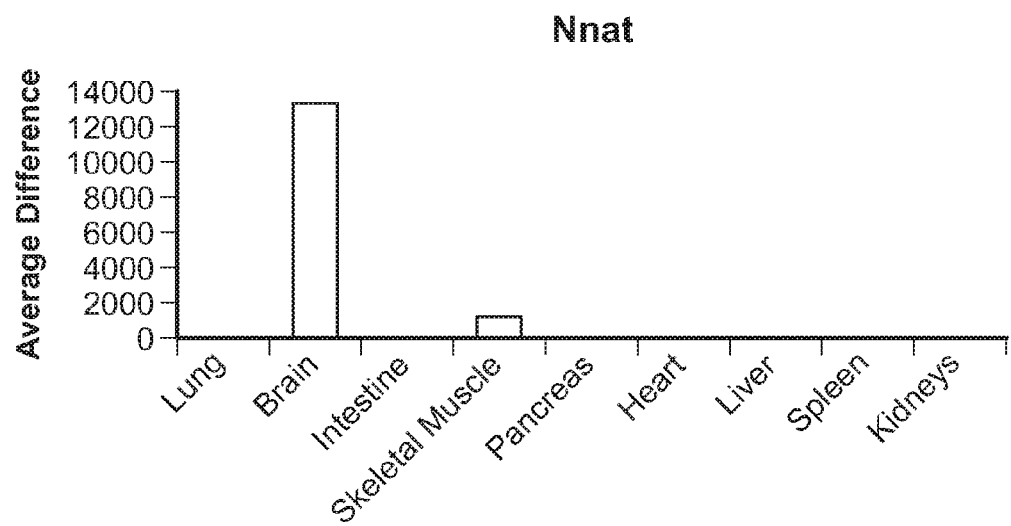
Figure 1R:
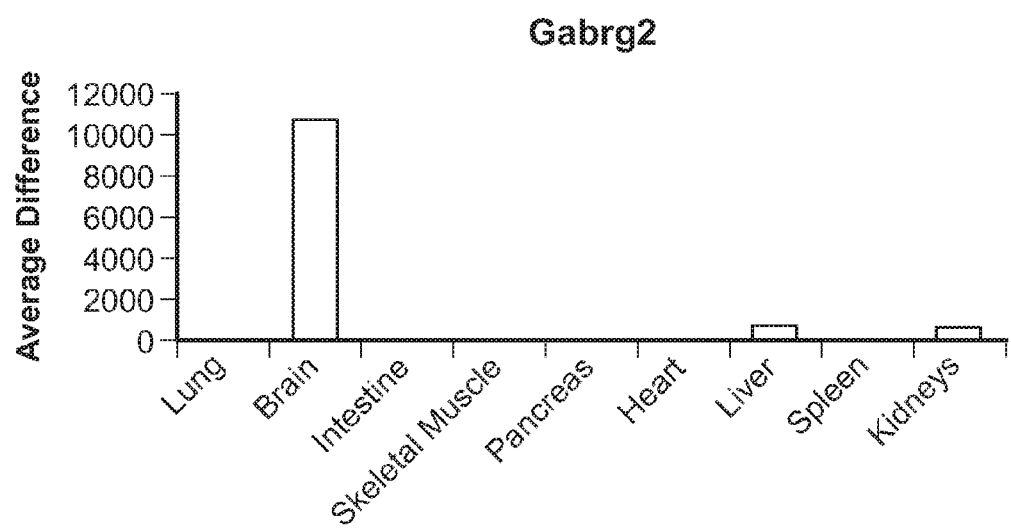
Figure 1S:
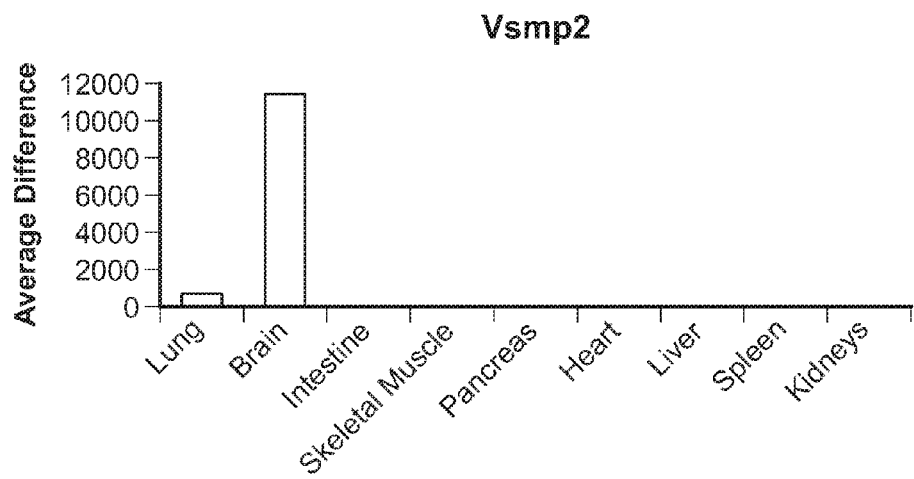
Figure 1T:
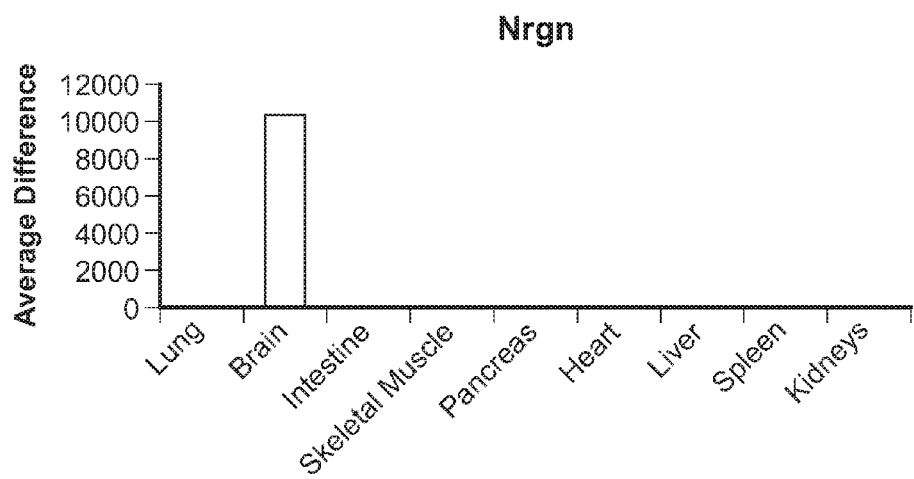

A graphical representation of the comparative expression levels of mRNA in fresh mouse brain as compared to other tissues is shown in FIGS. 1A and 1B for the final candidate genes shown in Table 1.

EXAMPLE 2

Preparation of Antibodies

Recombinant Proteins (Antigens)

Nucleotide sequences encoding marker proteins were inserted into pGEX or pET Vectors for production of protein in E. coli. Proteins from pET vectors were purified using Qiagen Ni-NTA following manufacturer's protocol (The Qiaexpressionist 06/2003; Qiaben, Valencia, Calif.). Those from the pGEX vector were purified using immobilized glutathione from Pierce (Rockford, Ill.) following manufacturer's protocol. In some cases plasmids were sent to GenWay Biotech, Inc. (San Diego, Calif.) for large scale production of protein from E. coli. These included: pET 100 GAD 67, pET 102 GAD 67, pET 28 Zygin, and Zygin I. Quality control included analysis on SDS-PAGE, N-terminal Edman sequencing and Mass Spectrometry as appropriate (Li, A., et al., (2003) Protein Expr Purif, 31(2):197-206). Protein concentration was estimated by Absorbance at 280 nm using calculated extinction coefficients from the protein sequence plus construct obtained at the Swiss-Prot web site and agreed with visual inspection of protein-stained bands on SDS-PAGE.

Animal Immunization and Antibody Characterization

Anti-peptide immunogens were prepared as in Li, A., et al., 2003 (supra). Rabbits were immunized at Harland Bio-products for Science, Inc. (Madison, Wis.). Rabbit serum was immunopurified over an affinity column containing the cognate peptide or protein antigen. Mice were immunized with 25 ug/mouse immunogen in MPL-TDM adjuvant (Sigma-Aldrich, St. Louis, Mo.) followed by at least 2 boosts in adjuvant and a $3^{rd}$ in PBS 3 days before fusion. Syrian hamsters were immunized with 100 ug/hamster in compete Freund's adjuvant followed by boosts in incomplete Freund's adjuvant and a final boost in PBS. All fusions were performed at Washington University School of Medicine Hybridoma Center. Monoclonal antibodies were purified from culture media on Protein A-agarose or Goat-a-Mouse IgG-agarose or produced in ascites by Maine Biotechnology (Portland, Me.). All purified Ab's were dialyzed vs. PBS/azide pH 7.2 and protein concentration was estimated from Absorbance at 280 nm using an extinction coefficient of 1.4 (liters/grams-cm). Subclass determination for monoclonal Ab's utilized the IsoStrip kit from Roche (Indianapolis, Ind.). Minimum epitope assignment was based on immunostaining of ABIMED spot peptide arrays prepared at the MIT Biopolymers Facility (Cambridge, Mass.). Each spot comprised a 10-mer contiguous peptide, and depending on the number of residues in the antigen of interest, either a one-, two-, or three-residue offset was used to cover the entire antigen sequence. For example, for a one-residue offset spot 1 contains sequence 1-10, spot 2 sequence 2-11, spot 3 sequence 3-12, etc.

Development of Antibodies Against Visinin-1 (VLP-1)

Monoclonal antibodies were raised against VLP-1 using a combination of DNA and protein injections. The vector VR1012 (Vical Inc.) and certain sequences from CTLA4Ig were used for the DNA injections. VR1012 has been optimized for protein expression in mouse skeletal muscle, whereas, sequences contained in CTLA4Ig were previously shown to greatly increase the antibody response in mice (Boyle, et al., Nature (1998) 392:408-411).

Standard procedures used at the Hybridoma Center at Washington University in St. Louis for the creation and maintenance of the fusions were followed.

TABLE 2

Antibodies to Marker Proteins

| Ab Designation | Species | Isotype | Immunogen | Epitope(s) |
|---|---|---|---|---|
| R3471 | Rabbit | IgG | VLP-1 DNA and | Major: aa 3-11, 16-23, 139-155 |
| 4399 3A8.1 | Mouse | IgG1K | GST-VLP-1 protein | Not established |
| 4403 2B9.3 | Mouse | IgG2aK | boost | Not established |
| 4421 2G10.2 | Mouse | IgG1K | Neuroserpin DNA | aa 145-154 |
| 4421 5B5.1 | Mouse | IgG1K | &GST-Neuroserpin | aa 370-379 |
| 4421 7D6.3 | Mouse | IgG2aK | protein boost | Not established |
| 4505 2F1.1 | Mouse | IgG1K | " | aa 193-202 |
| 4554 1G4.4 | Mouse | IgG1K | pET28-Zygin | aa 23-28 |
| 4563 4G3.1 | Hamster | IgG1 | pET28-Zygin | aa 7-12 |
| R4726 | Rabbit | IgG | pET28-Zygin | Not determined |
| R4727 | Rabbit | IgG | pET28-Zygin | Not determined |
| R4610 | Rabbit | IgG | GAD 67 | Multiple epitopes |
| R4609 | Rabbit | IgG | GAD 67 | Multiple epitopes |
| R4043 | Rabbit | IgG | GAD 67 peptide(61-79) | assumed aa 61-79 |
| R4044 | Rabbit | IgG | GAD 67 peptide(79-97) | assumed aa 79-97 |
| Chemicon MAB 5406 (purchased) | Mouse | IgG2aK | r-rat GAD 67 | aa 13-25 |
| SC-7571 | Goat | IgG | internexin | N-terminus |
| SC-7570 | Goat | IgG | internexin | C-terminus |
| SC-7538 | Goat | IgG | Synaptosomal-associated protein-25 kD | N-terminus |
| SC-7539 | Goat | IgG | Synaptosomal-associated protein-25 kD | C-terminus |
| SC-20038 | Mouse | IgG1K | Crude brain extract | Not determined |
| SC-23570 | Goat | IgG | Proteolipid protein 1 | N-terminus |
| SC-18529 | Goat | IgG | Proteolipid protein 1 | Internal peptide |
| SC-14250 | Goat | IgG | Myelin-associated oligodendrocyte | Internal peptide |
| SC-25666 | Rabbit | IgG | basic protein | Not known |

SC - antibodies obtained commercially from Santa Cruz
Mouse and hamster antibodies are monoclonal while the rabbit antibodies are polyclonal and immunopurified.
GAD67 = glutamate decarboxylase 1 (brain, 67 kD)
Internexin = internexin neuronal intermediate filament protein, alpha

EXAMPLE 3

Figure 3C:
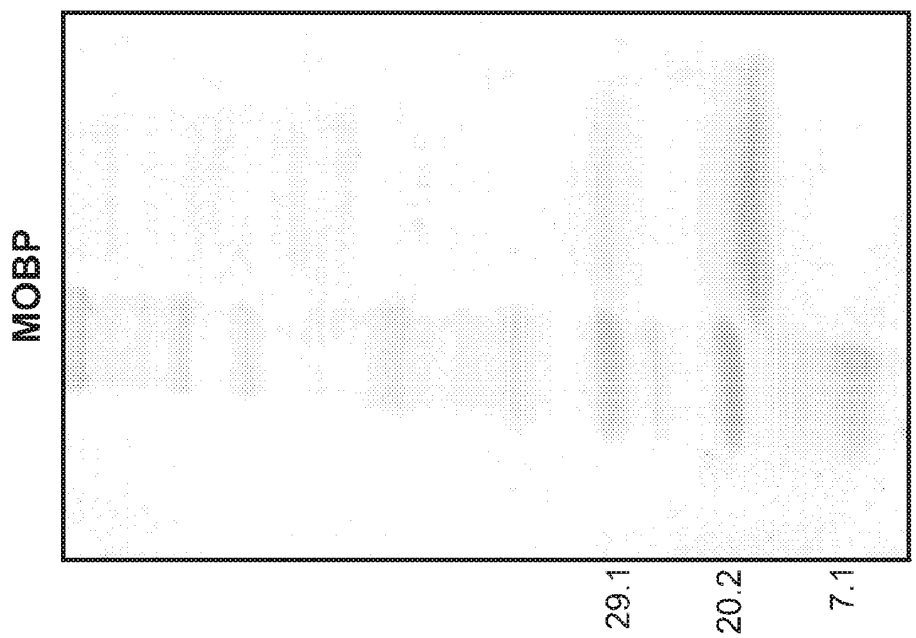
FIGS. 3A-C show Western blots demonstrating the presence of the protein expression product of genes INA, SNAP25, and MOBP. PLP-1 did not show protein expression detectable by this method.
Figure 3B:
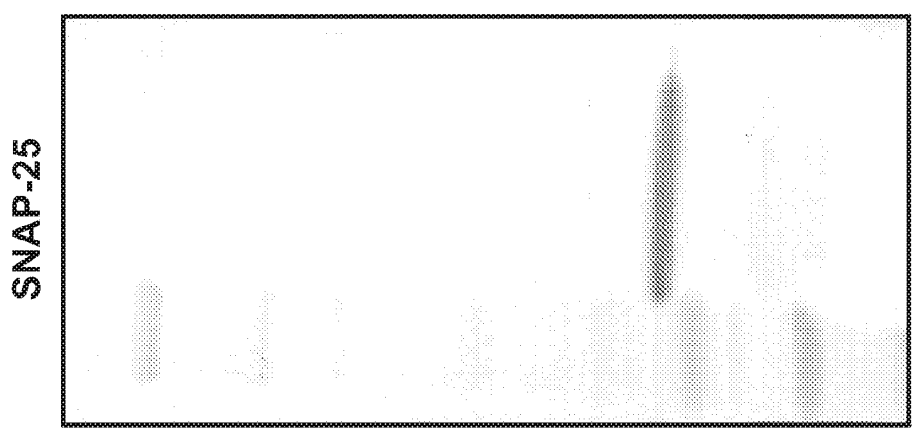
Figure 3A:
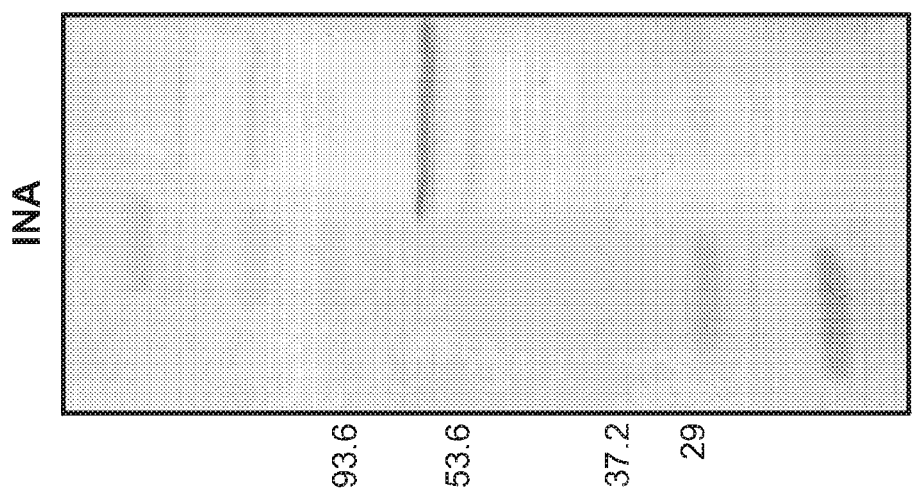

Assessment of Proteins Expressed by the Candidate Genes for Identifying Brain Injury Some of the proteins expressed by the candidate genes were tested for their presence in human brain by Western blot. Normal Human Brain homogenate (GenoTechnology, Inc., St. Louis, Mo.) was loaded at 75 µg, electrophoresed on 4-20% SDS-PAGE and electrotransferred to PVDF. Molecular weight standards were also run to establish the expected region of the brain protein being assessed. All primary Ab concentrations at 2 µg/ml for 2 h, secondary antibody coupled to alkaline phosphatase at $\frac{1}{1000}$ for 1 h, with varying substrate development times. FIG. 2 shows a composite Western blot clearly showing the presence of proteins encoded by the genes for VSNL1, FEZ1, SERPINI1, and GAD1. The primary antibody used for the Western blot is noted. FIG. 3 shows a composite western blot for the presence of proteins encoded by the genes for INA, SNAP-25 and MOBP. All the encoded proteins except that code by PLP1 were clearly present in brain tissue.

EXAMPLE 4

Enhanced Abundance of Candidate Biomarkers in Brain Compared to Other Tissues

The presence of protein expressed by some of the candidate genes were assessed in various tissues. A Western blot was performed on a human tissue array, (GenoTechnology, Inc. 50 µg per tissue). The human tissue array included liver, brain, lung, kidney, spleen, testis, ovary, heart, pancreas, uterus, breast, cervix, rectum, prostate, thyroid, laryngopharynx, stomach, and skin. For human VLP-1, there is high protein expression in brain with far less in cervix and some in skin. The lack of protein expression in the other tissues is consistent with the mRNA expression data. For neuroserpin, some protein was found in prostate, and thyroid, but far less than brain, and a trace in kidney and pancreas. The protein gene product encoded by SNAP-25 was found in abundance in brain with only trace amounts in a few other tissues. Likewise for the protein encoded by MOBP; only a very trace amount was found in pancreas. Zygin and GAD67 protein expression occurs only in brain tissue and not in any of the other tissues tested.

EXAMPLE 5

Determination of Visinin-Like I in Stroke Patients

Blood was retrospectively collected from clinical laboratory specimens that were available from a group of patients who presented to Barnes-Jewish Hospital (BJH) with an acute neurological deficit between March and November of 2002. These patients had a discharge diagnosis of ischemic stroke. Patients who did not have a clear time of stroke onset were excluded. Eighteen patients met these criterion and were tested.

Plasma from the blood samples was subjected to the following procedure to determine the level of visinin like 1

(VLP-1). Electrochemiluminescence on the Meso Scale Discovery (MSD) equipment was used. The procedure is as follows:

Day 1
1. Coat MSD regular binding plate with 5 µl/well of 60 µg/ml of monoclonal antibody 3A8.1. Leave plate uncovered and allow samples to dry overnight at room temperature.

Day 2
2. Add 200 µl of TBS-Casein (0.1% Tween 20) and incubate plate at room temperature for 2 hours while shaking.
3. Wash plate with 300 µl TBS (0.1% Tween 20) buffer twice. Aspirate or decant buffer.
4. Dilute VLP-1 standards in pooled normal heparinized plasma or serum.
5. Prepare standards, QCs, and samples as follows:
   110 µl plasma/serum
   44 µl HBR reagent (2 mg/ml)
   66 µA TBS-Casein (0.1% Tween 20)
   Mix well and add 100 µA of standards, QCs, and samples into each well. Incubate overnight at 4° C. while shaking.

Day 3
6. Wash the plate 3 times with 300 µA TBS (0.1% Tween 20) buffer.
7. Add 100 µA 4.5 µg/ml Ruthenium labeled-rabbit anti VLP-1 (R3471) (labeled at a ratio of 20:1) in TBS-Casein (0.1% Tween 20). Incubate for 2 hours at room temperature while shaking.
8. Wash the plate 3 times with 300 µA TBS (0.1% Tween 20) buffer.
9. Add 150 µA of 1× Read Buffer T.
10. Read plate with the Sector Imager instrument from MSD.

The concentrations of coating and detection antibodies listed above were found to give the highest sensitivity of all the concentrations tested.

Figure 4A:
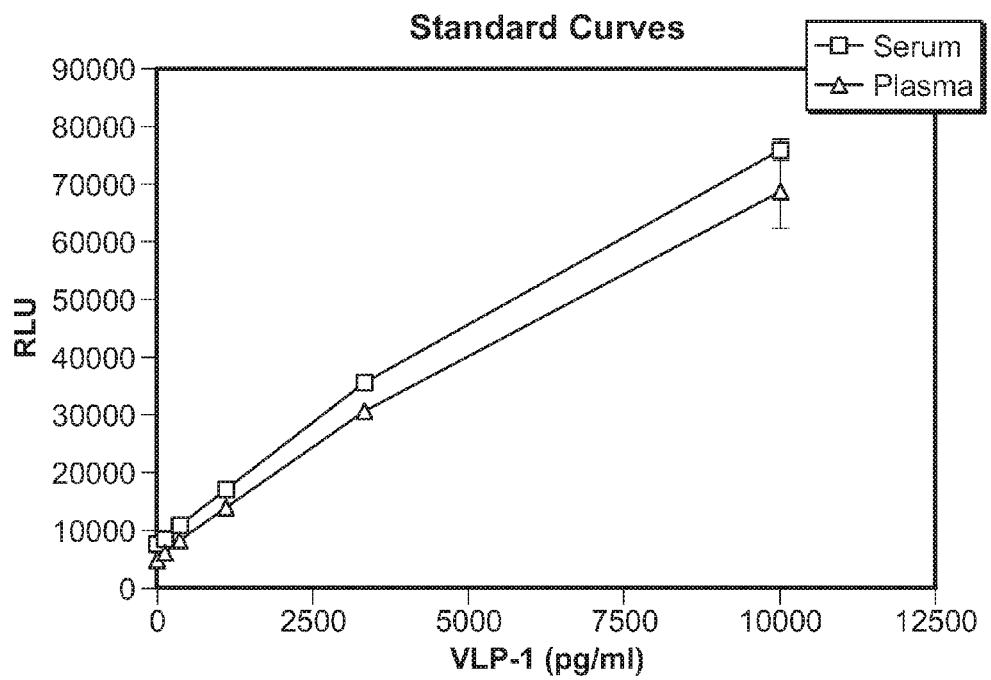
FIGS. 4A and 4B show standard curves for the VLP-1 sandwich assay.
Figure 4B:
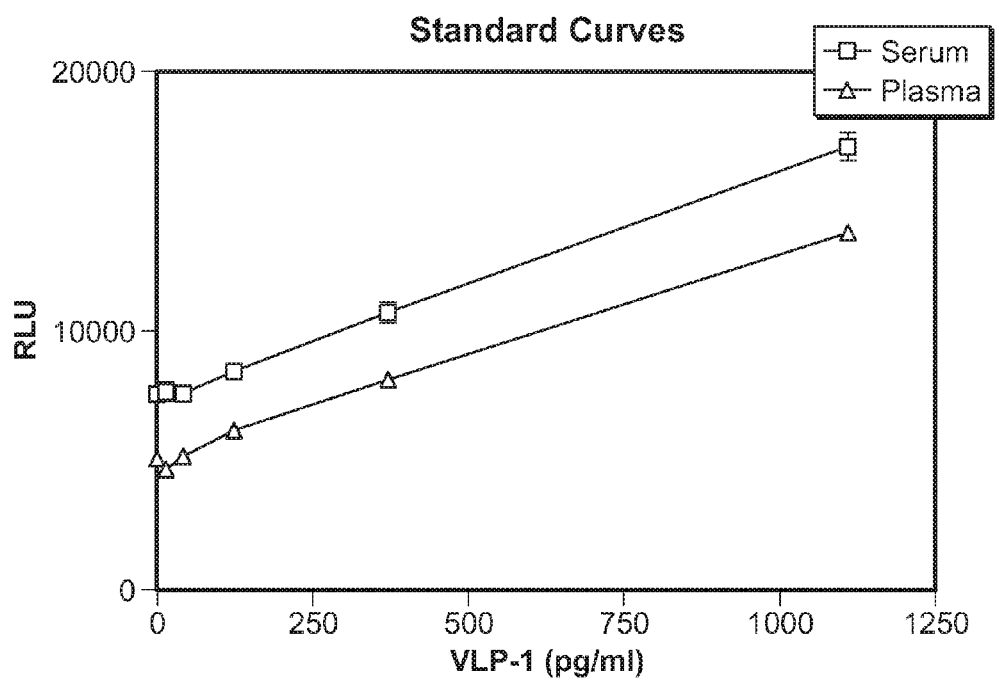
Figure 5A:
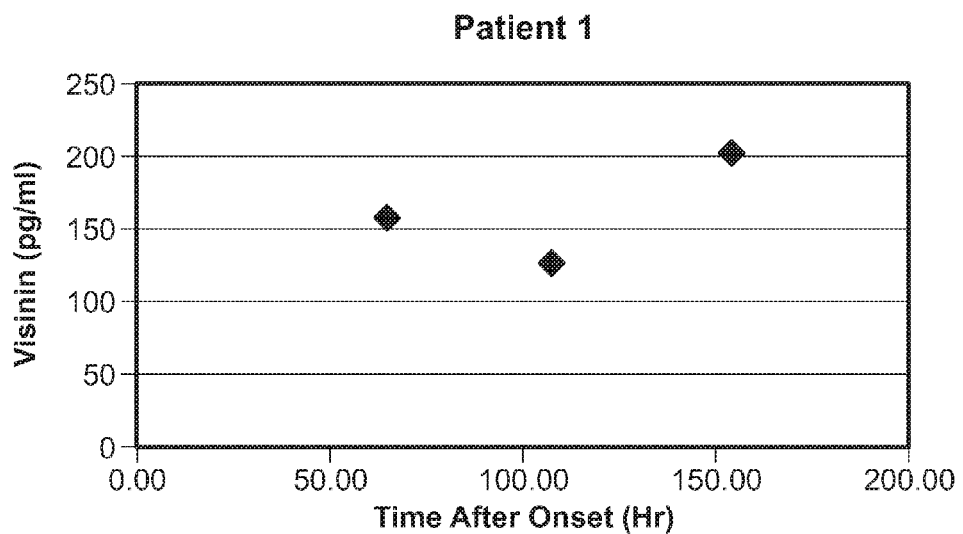
FIGS. 5A-5R show the results of determination of VLP-1 protein in the plasma of blood samples taken from patients diagnosed as having suffered ischemic stroke.
Figure 5B:
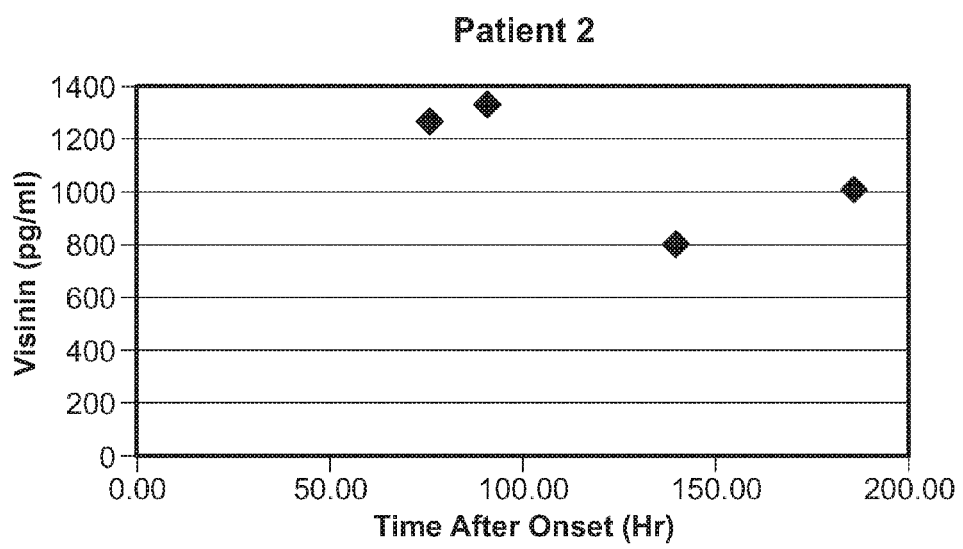
Figure 5C:
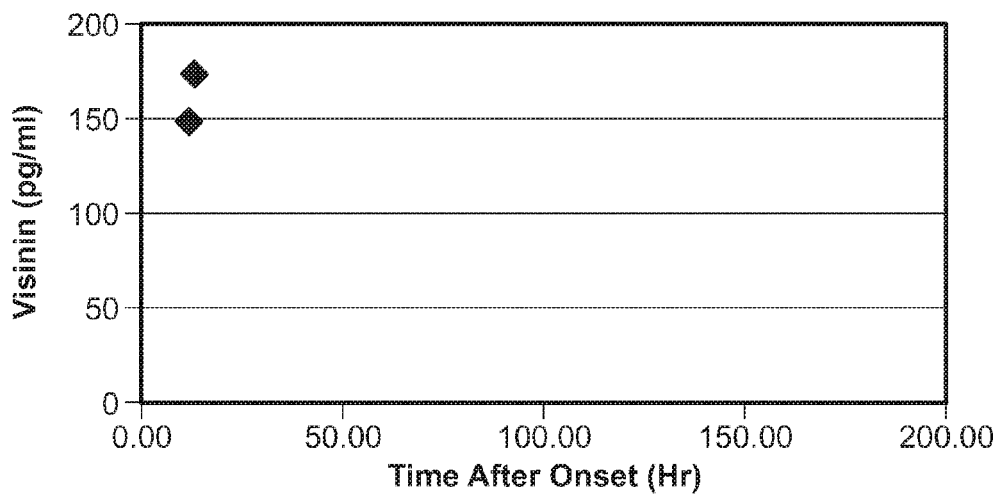
Figure 5D:
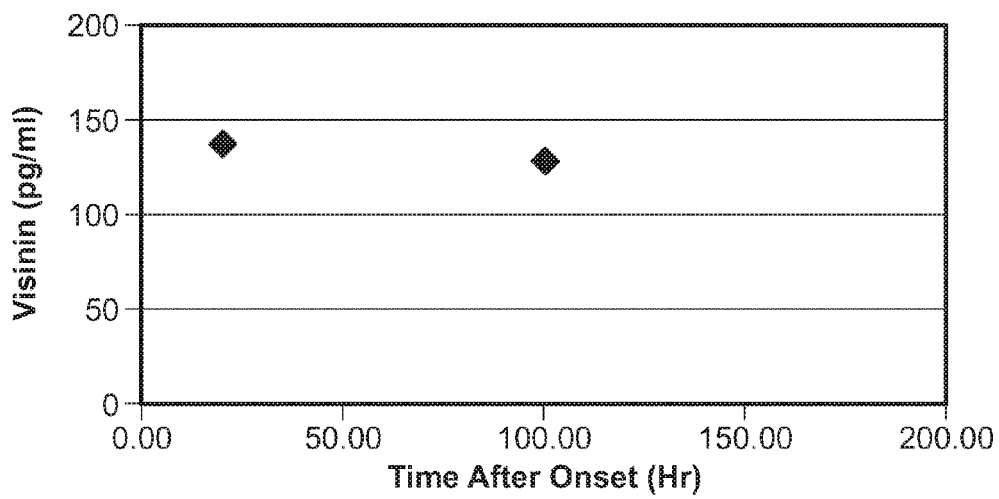
Figure 5E:
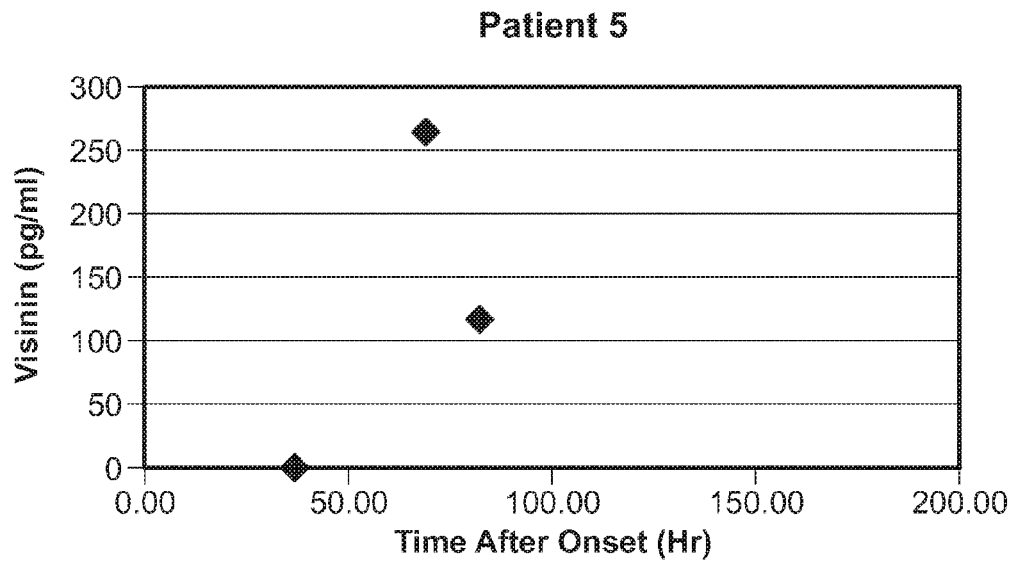
Figure 5F:
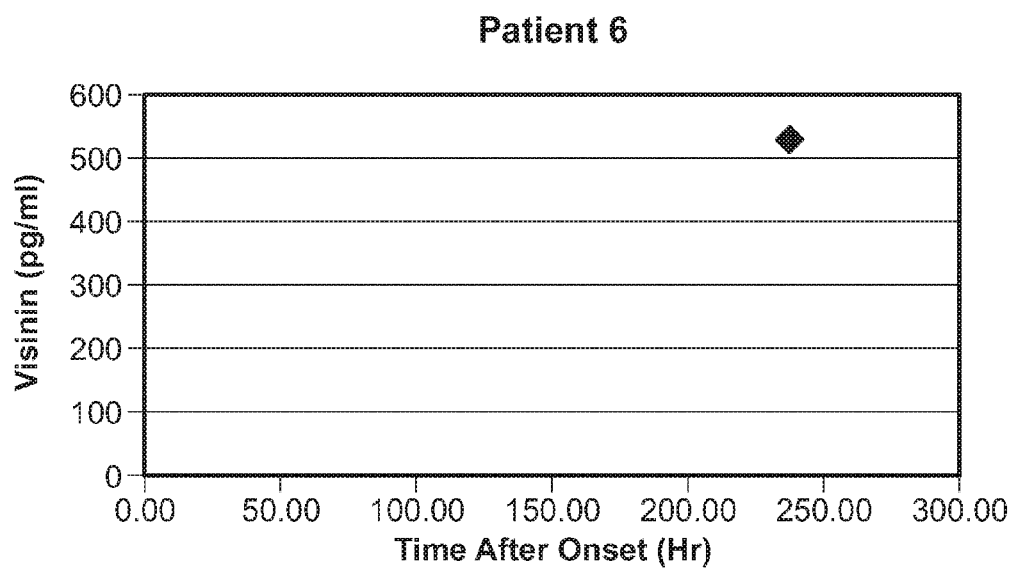
Figure 5G:
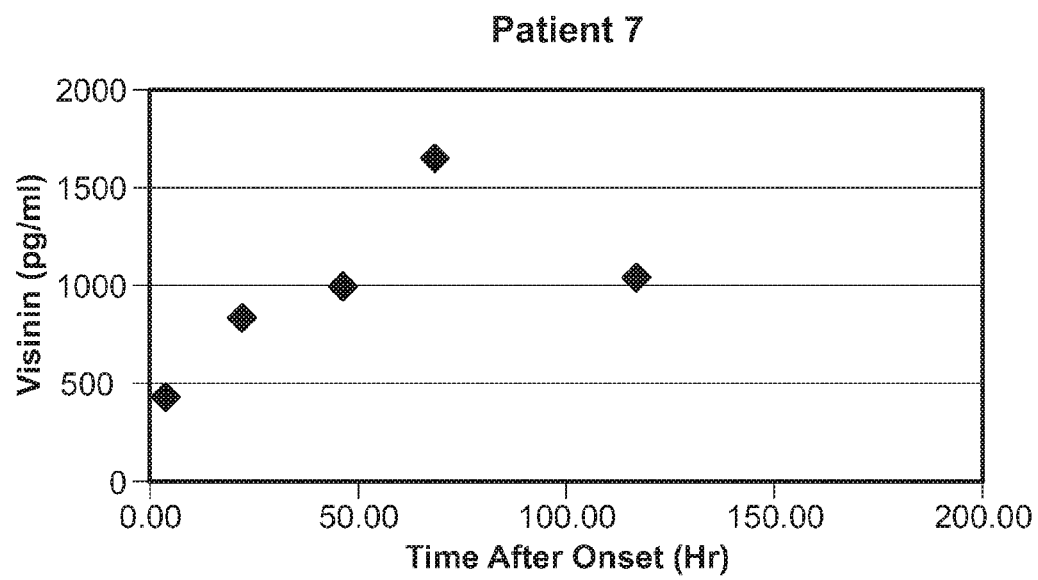
Figure 5H:
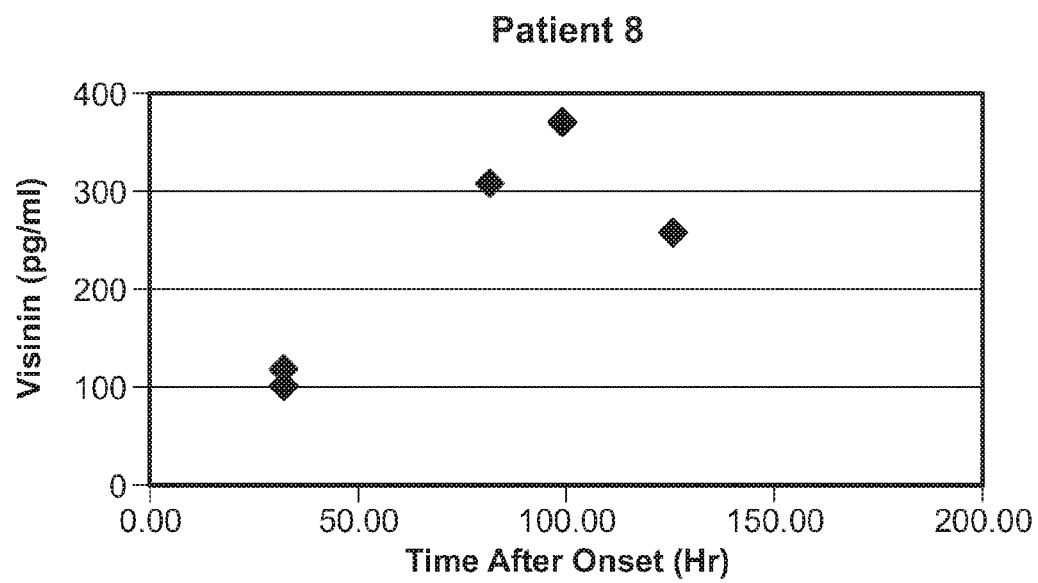
Figure 5I:
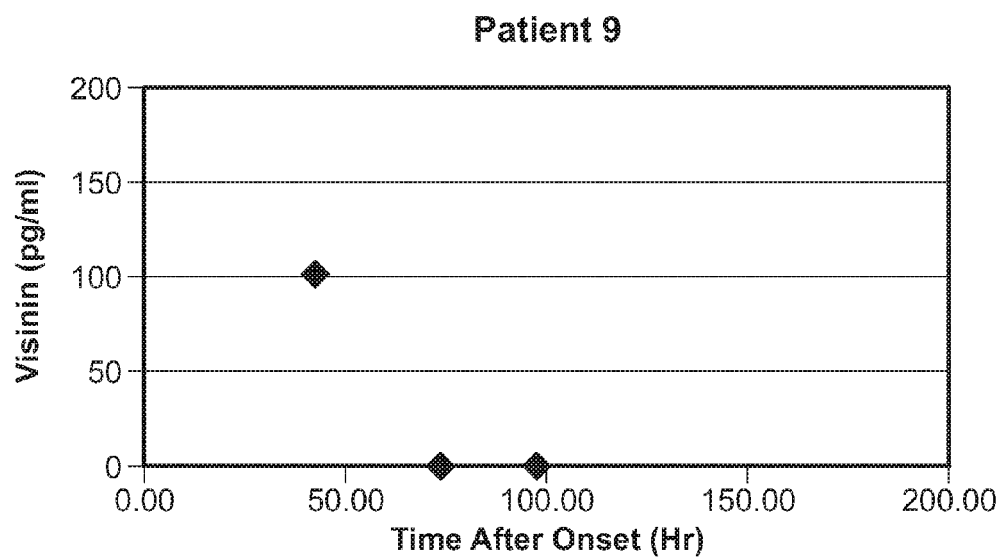
Figure 5J:
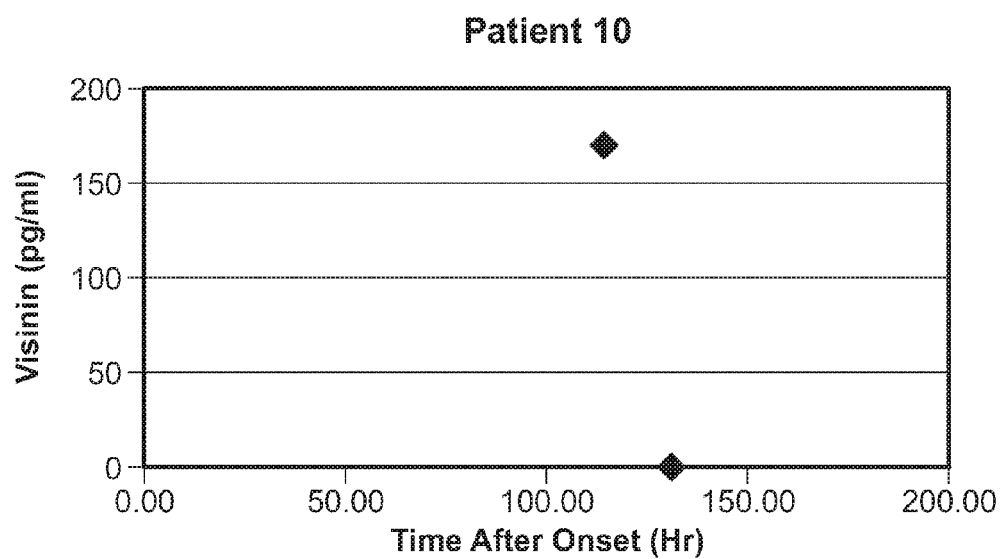
Figure 5K:
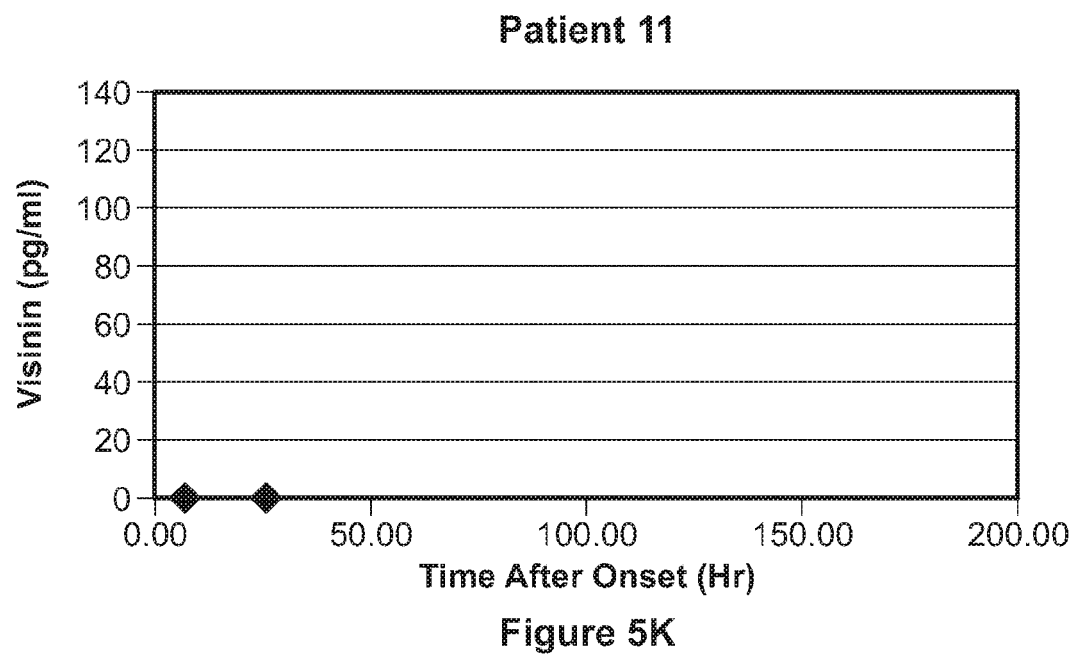
Figure 5L:
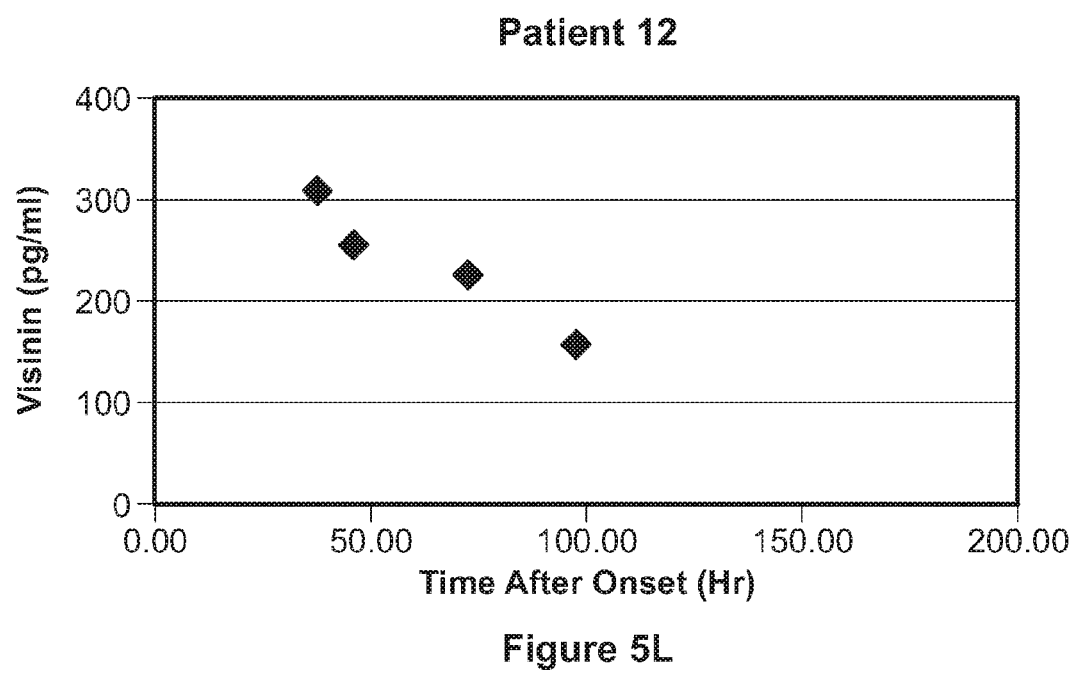
Figure 5M:
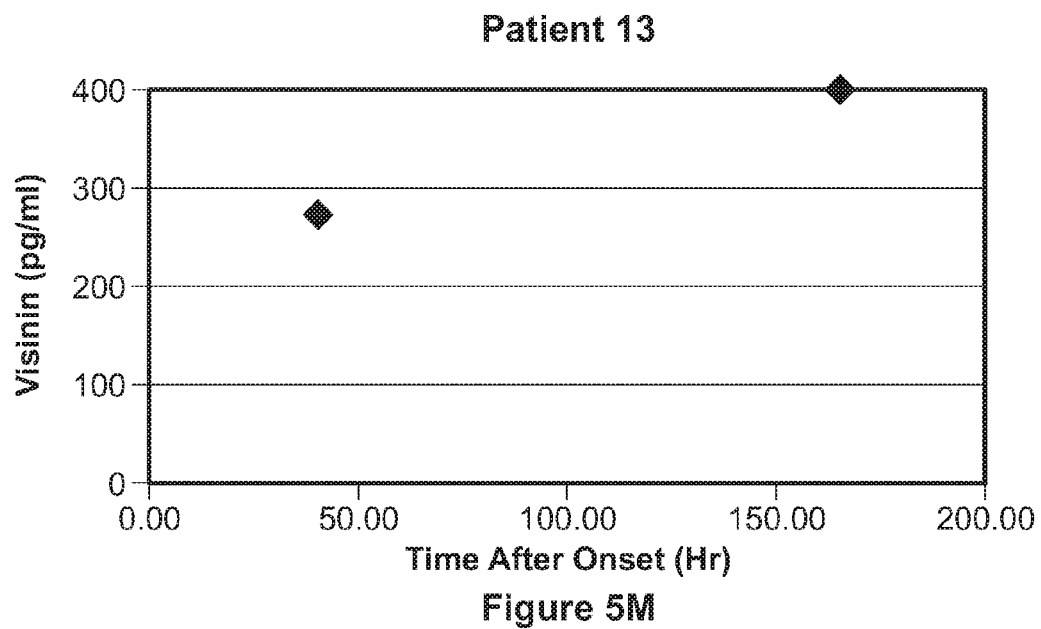
Figure 5N:
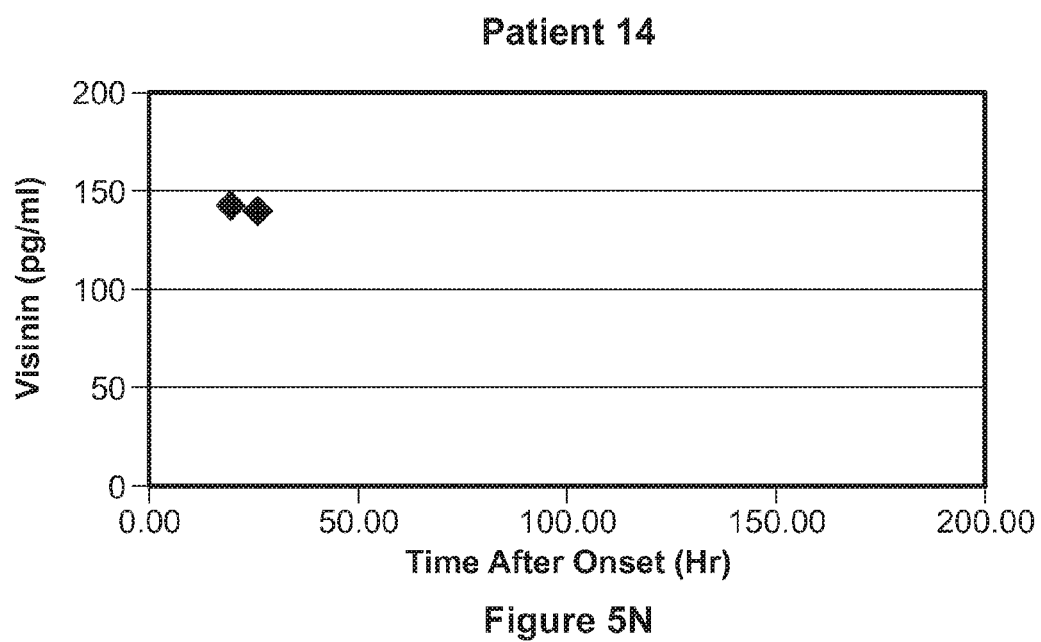
Figure 5O:
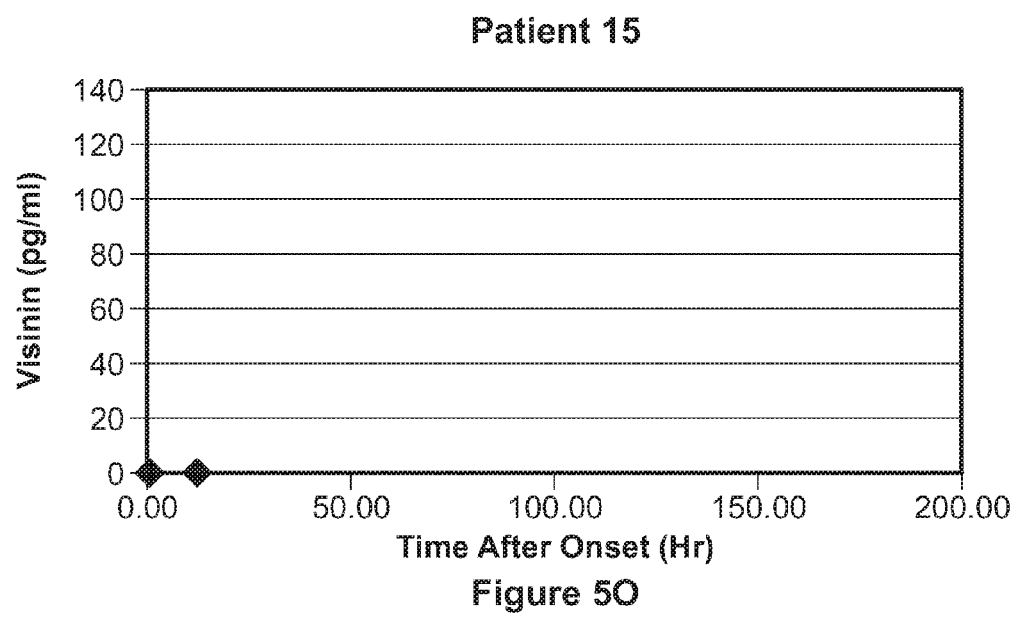
Figure 5P:
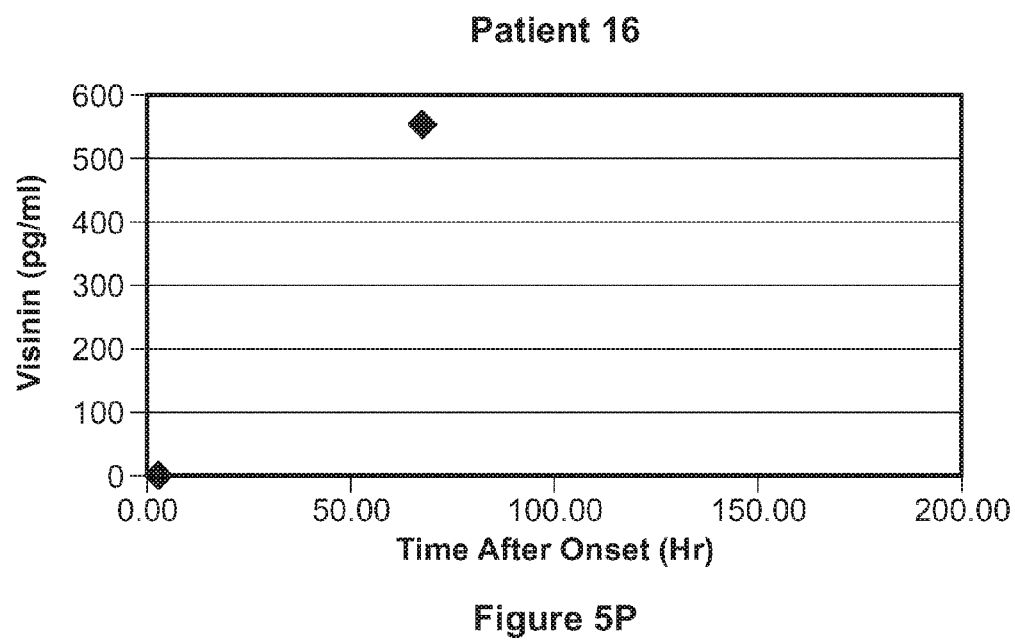
Figure 5Q:
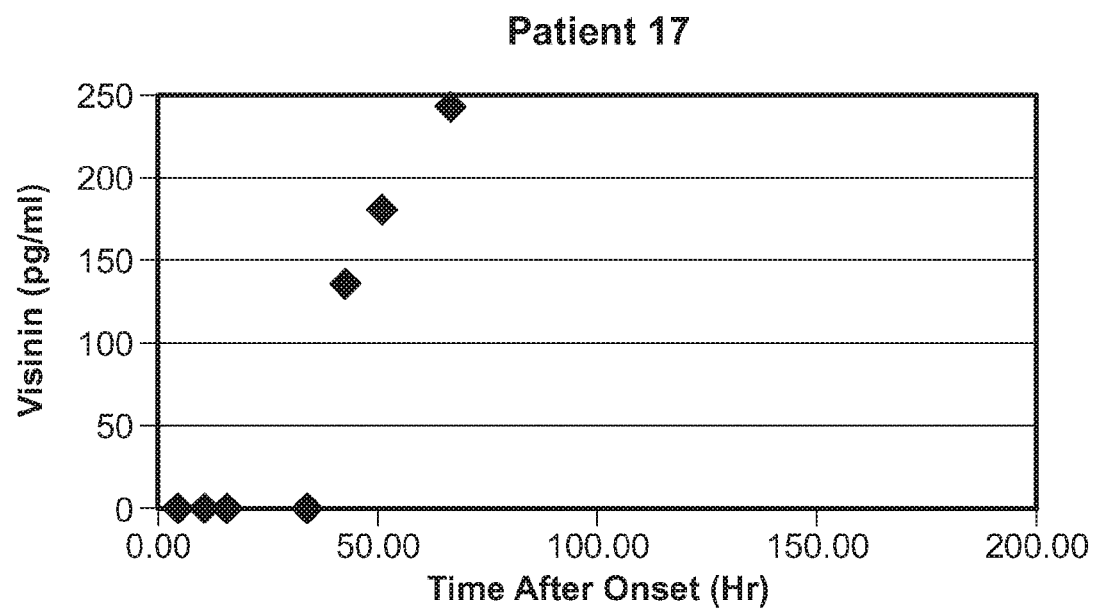
Figure 5R:
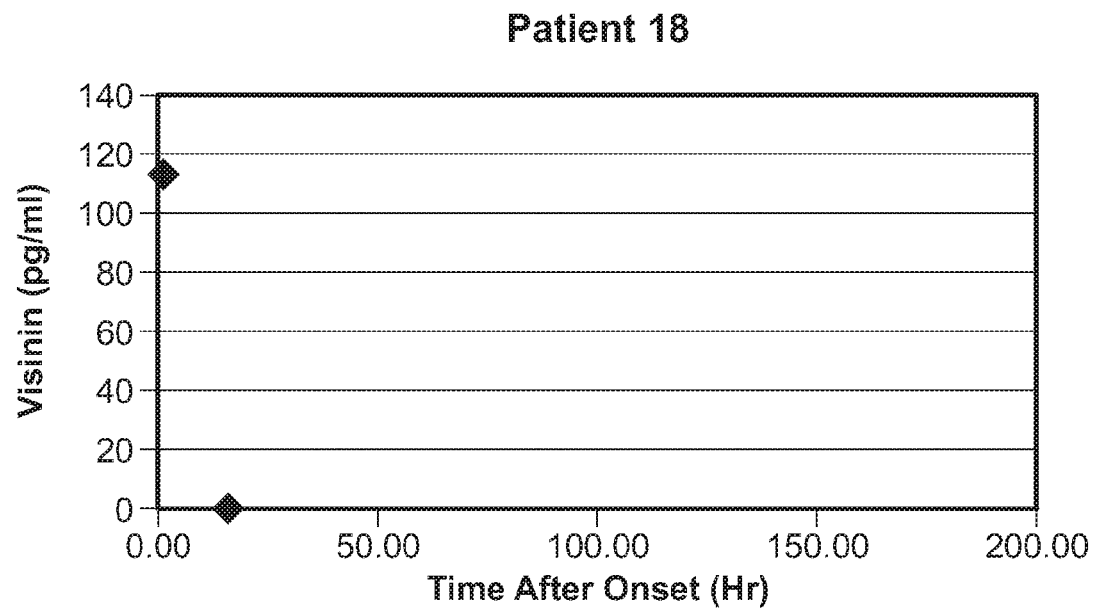

Standards between 13.7 and 10,000 pg/ml were prepared by spiking recombinant VLP-1 into a pool of normal plasma. FIGS. 4A and 4B show a typical standard curve generated via a 4-parameter curve-fitting software. FIG. 4A shows the range up to 12,500 pg/ml; panel B shows an expanded depiction of the standard curve in the region from 0-1,250 pg/ml. "RLU" refers to relative light units. The sensitivity of the assay (lowest measurable amount) was estimated as 41.1 pg/ml based on the assay blank+3 standard deviations.

Thirty-nine plasma samples from normal donors were analyzed and 36 of them were below the limit of detection; the others had low values of 42.3, 83.6, and 104.6 pg/ml. Of the 18 patients with confirmed stroke, only two had no samples with detectable VLP-1, with most considerably higher. FIGS. 5A-5E show the results in pg/ml at various times after stroke onset for the 18 patients.

EXAMPLE 6

Rat Stroke Model

A rat stroke model was employed to assess the time course of appearance of visinin-like 1 in the blood and cerebrospinal fluid, as a function of time.

A Permanent Middle Cerebral Artery Occlusion (pMCAO) Filament Model of Stroke was used. Ischemia was induced in femoral vein cannulated male Sprague-Dawley rats (Charles-River) using the permanent middle cerebral artery occlusion (pMCAO) intra-luminal filament method. In brief, a midline incision was performed and the right common, internal, and external carotid arteries were exposed. The external carotid and occipital arteries were ligated. The common carotid artery was ligated, and the internal carotid artery was temporarily closed. A small incision was made in the common carotid artery and a filament (3.0 Ethilon; heat blunted tip) was inserted into the internal carotid artery through the common carotid artery. The filament was advanced 17.5 mm to occlude the origin of the MCA. The filament was secured in place in the right common carotid artery using a surgical nylon suture. After surgery, anesthesia (isoflurane) was discontinued and the animals were allowed to recover.

Blood was collected (approximately 0.25 ml) at 5 time-points (24 hours before surgery as well as 1, 4, 8, and 24 hours post-occlusion). The blood was allowed to clot at room temperature and subsequently centrifuged in order to collect serum samples. CSF was collected 24 hours post-occlusion. All samples were coded before assay, according to the following protocol.

1. Dilute standards
2. Wash the plate that had been coated with mAb 3A8.1 3 times with 300 µl TBS-TBuffer per well. Aspirate excess buffer after the third wash.
3. Add 100 µl (CSF assay) or 150 µl (serum assay) standards, QCs, and samples to wells. Cover plate with plate sealer and shake briefly. Incubate at shaking at room temperature for 2 hours (CSF assay) or overnight shaking at 4° C. (serum assay). Samples for the CSF assay are run undiluted, whereas samples for the serum assay are run diluted 1:3 in assay buffer.
4. Prepare 0.1 µg/ml biotin-2B9.3 (CSF assay) or 0.5 µg/ml Biotin-rabbit anti VLP-1 (serum assay) in Blocking Buffer.
5. Decant liquid from plate and tap out excess fluid. Make sure all fluid is out of wells.
6. Wash the plate 4 times with 300 µl TBS-TBuffer per well. Aspirate excess buffer after the fourth wash.
7. Immediately add 100 µl 0.1 µg/ml Biotin-2B9.3 anti VLP-1 (CSF assay) or 0.5 µg/ml Biotin-rabbit anti VLP-1 (serum assay) to each well. Incubate 2 hours at 37° C.
8. Prepare 0.5 µg/ml Streptavidin-Alk-Phos by diluting 1:1000:0.5 mg/ml stock in glycerol with Blocking Buffer.
9. Decant liquid from plate and tap out excess fluid. Make sure all fluid is out of wells.
10. Wash the plate 4 times with 300 µl TBS-T Buffer per well. Aspirate excess buffer after the fourth wash.
11. Add 100 µl 0.5 µg/ml Streptavidin-Alk-Phos to each well. Incubate 1.5 hours at 37° C. Decant liquid from plate and tap out excess fluid. Make sure all fluid is out of wells.
12. Wash the plate 4 times with 300 µl TBS-T Buffer per well. Aspirate excess buffer after the fourth wash.
13. Immediately add 100 µl CDP-Star substrate to each well.
14. Read plate 5-10 minutes at 460/40 nm.

Figure 6:
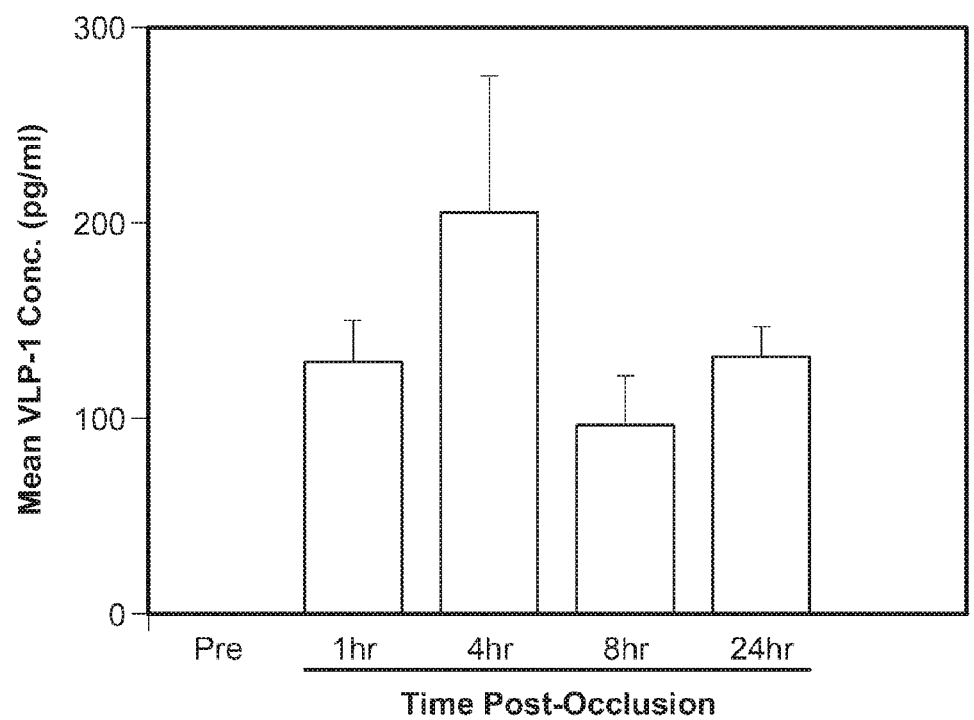
FIG. 6 shows the results of assays of rat serum in a rat stroke model assayed for VLP-1.

The time course of visinin in serum according to this assay in the rat model is shown in FIG. 6. Prior to inducing the stroke, the values were undetectable. As shown, VLP-1 was detectable by one hour post-occlusion and was maintained for 24 hours. Similar assays in cerebrospinal fluid showed mean values in a five-rat sample of >20,000 pg/ml after 24 hours.

EXAMPLE 7

Development of Additional Assays

Quantitative assays were also developed for neuroserpin, GAD67, and zygin.

Figure 7A:
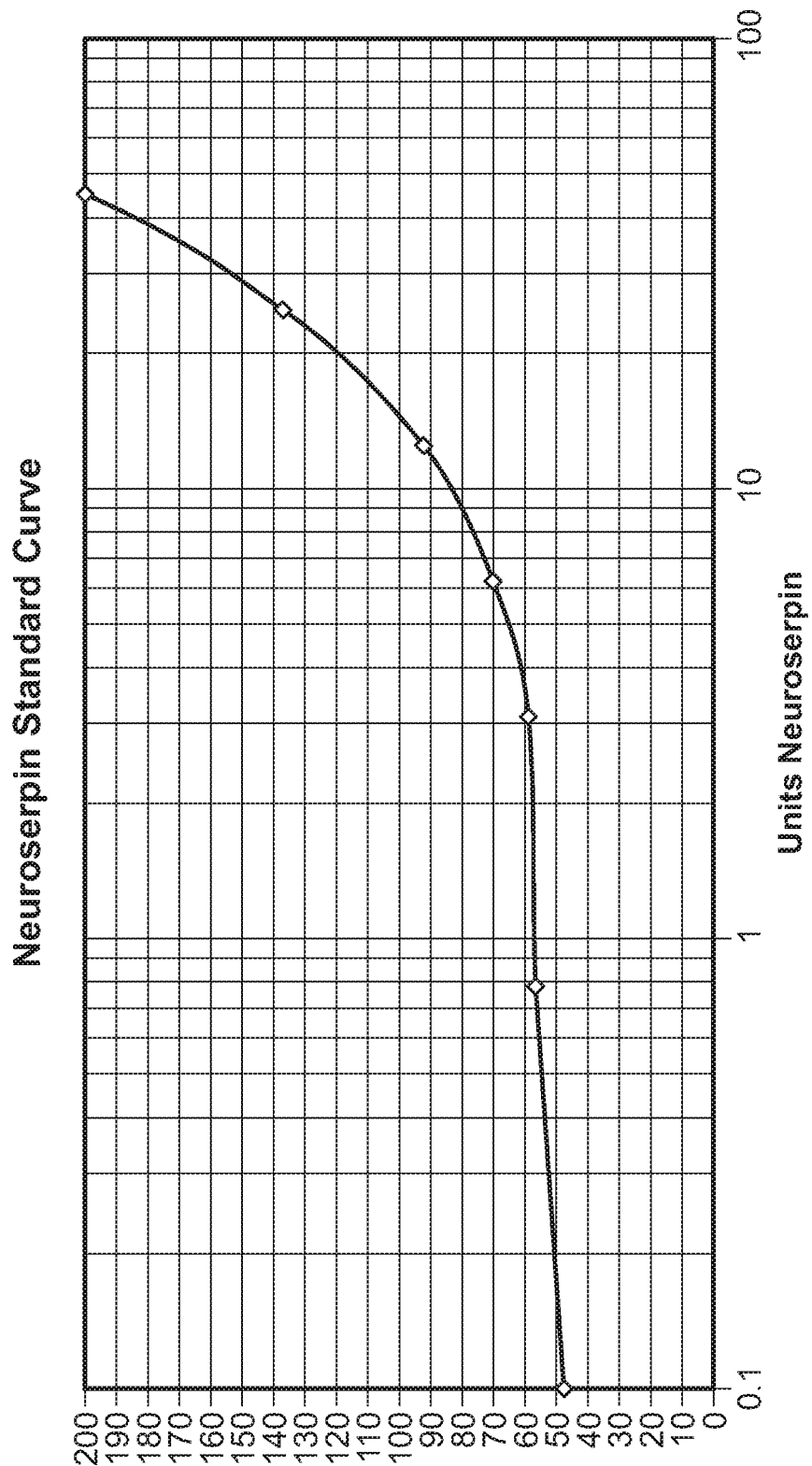
FIGS. 7A-7C show standard curves for sandwich assays developed for neuroserpin, GAD67 and zygin, respectively.

The assay for neuroserpin utilized capture antibody 4221 5B5.1 (coated at 3 µg/ml) and 2 µg/ml biotinylated 4505 2F1.1. Detection was via streptavidin-alkaline phosphatase. (See FIG. 7A.) Serpin was detected in 5 of 6 CSF samples from a rat model of ischemic stroke. The values ranged from 7 to 20 units of serpin.

Figure 7B:
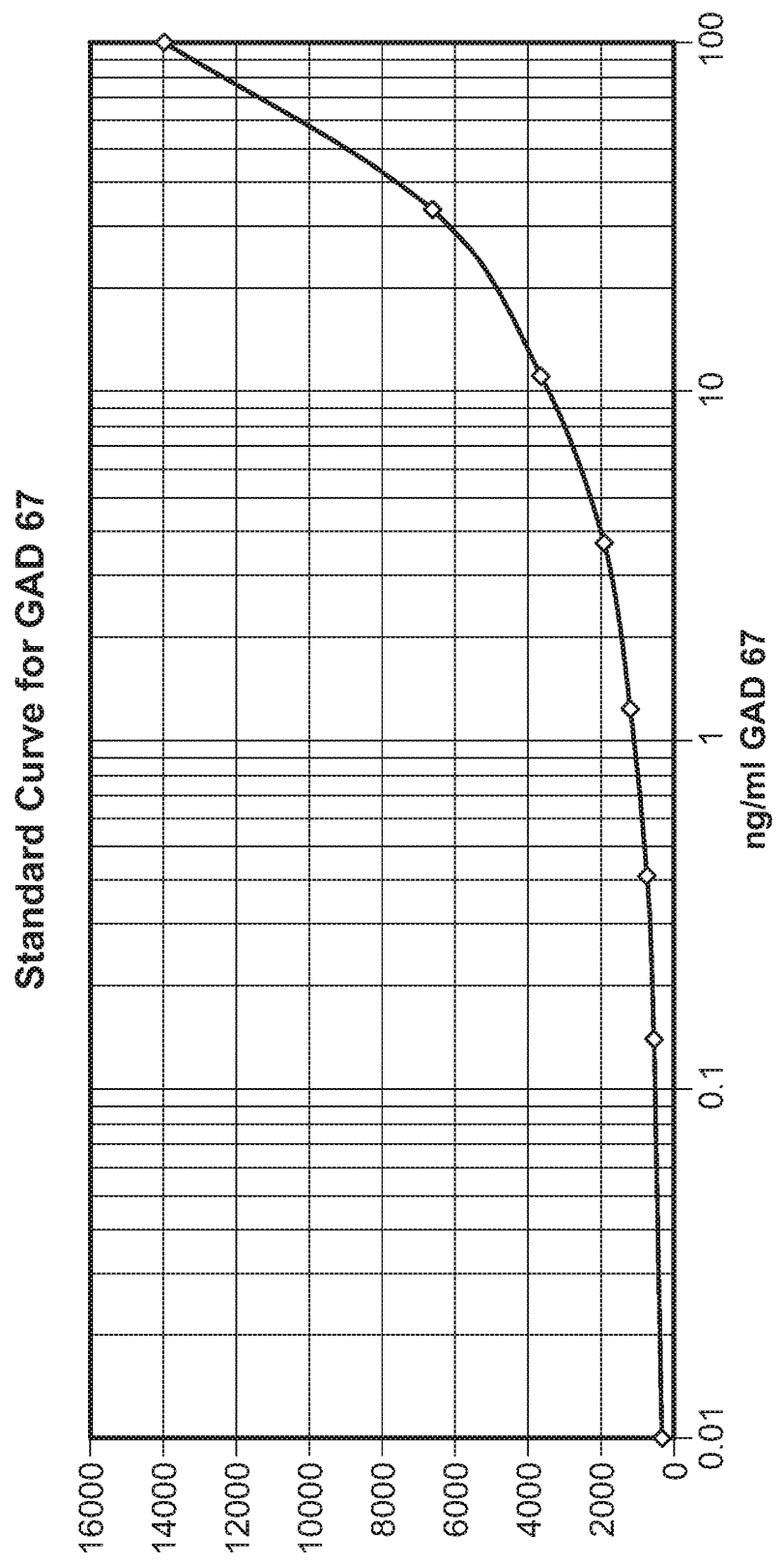

A quantitative assay for GAD67 was developed utilizing electrochemiluminescence (MESO Scale Discovery). The assay utilized immunopurified rabbit anti-GAD67 (R4043) as a capture antibody and Ruthenium labeled immunopurified rabbit anti-GAD67 (R4610) as a capping antibody. The standard curve gives a signal value of about 1,000 units at a concentration of 1 ng/ml GAD67 and a non-linear progression to about 14,000 signal units at 100 ng/ml. (See FIG. 7B.)

Figure 7C:
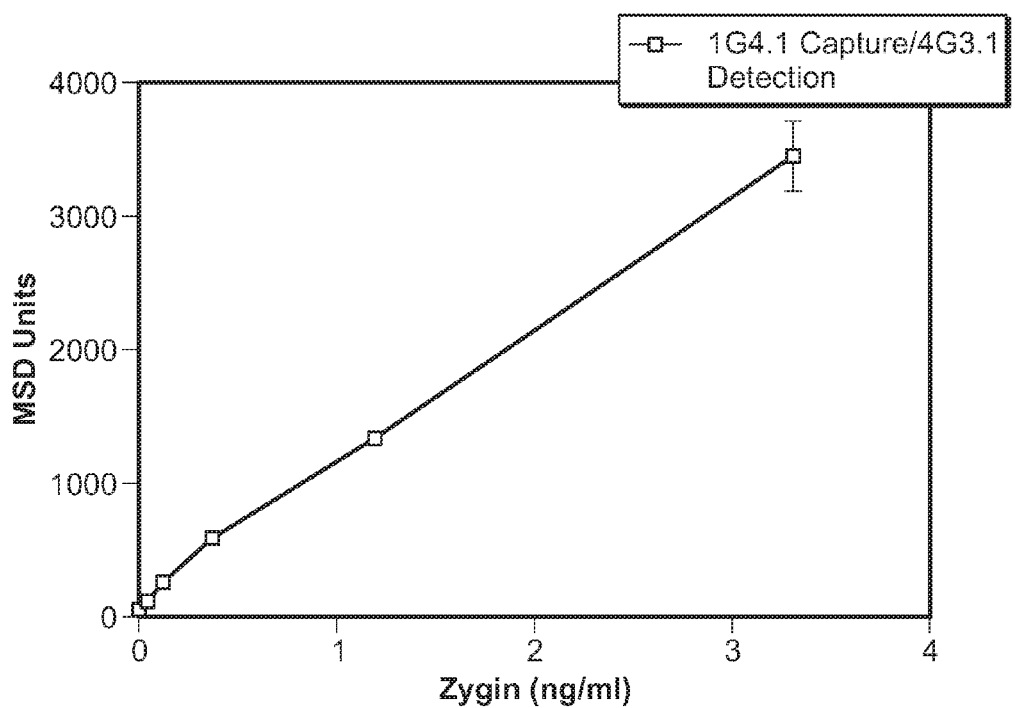

A quantitative assay for zygin was developed utilizing electrochemiluminescence (MESO Scale Discovery). The assay uses monoclonal antibody 1G4.4 as a capture antibody (300 ng coated on to MSD plates) and Ruthenium labeled monoclonal antibody 4G3.1 as a detection antibody. The standard curve (FIG. 7C) provides a general linear relationship of between 1,000 MSD units at 1 ng/ml to about 3,500 MSD units at 3 ng/ml.

EXAMPLE 8

Postmortem CSF Samples

A human CSF postmortem sample (Analytical Biological Services, Wilmington, Del.) was analyzed to determine if some of the brain markers would be found in CSF from brains deprived of oxygen for hours.

Western blots were performed on human postmortem spinal fluid at various dilutions and the intensity of the band compared visually with standards of the respective proteins. Values for zygin, neuroserpin and GAD67 were less than 2.5 ng/ml and visinin was between 25 and 250 ng/ml. This range was in good agreement with the quantitative assay determination of 17.1 ng/ml for visinin (4 pre-mortem CSF samples obtained from Teragenix had values ranging only from 0.11 ng/ml to 0.31 ng/ml). The quantitative system also detected GAD67 at 300 pg/ml and zygin at 56 pg/ml in the postmortem spinal fluid.

Summary of Results

Table 3 shows a summary of the results set forth above as determined for certain of the marker proteins.

TABLE 3

Protein Expression of Some Brain-Specific Genes*

| Gene | Western Blot of Human Brain | Other Human Tissues | Found in Human Blood After Ischemic Stroke | Postmortem Human CSF | Rat Stroke Model CSF |
|---|---|---|---|---|---|
| VSNL1 | + | Cervix, skin | Yes | Yes | Yes |
| FEZ1 | + | None | | Yes | |
| SERPINI1 | + | Prostate, thyroid and trace in kidney and pancreas | | | Yes |
| GAD1 | + | None | | Yes | |
| INA | + | | | | |
| SNAP25 | + | Trace in a few other tissues | | | |
| MOBP | + | Trace in pancreas | | | |
| PLP1 | Neg | | | | |

*Areas not filled in were not done.

The proteins expressed by the brain-specific genes are found in significant amounts in the brain and only slightly, if at all, in other tissues. The proteins tested were also found in blood after stroke in humans or in blood and/or CSF in a rat model of stroke. Thus, the protein products of the brain-specific genes give similar findings as the mRNA expression of the genes.

The invention claimed is:

1. A method to detect brain damage caused by Alzheimer's Disease in a test subject which method consists essentially of treating cerebral spinal fluid (CSF) of said subject with antibodies or fragments thereof specifically reactive with protein kinase C substrate RC3 (neurogranin) to form a sandwich of a capture antibody and a labeled antibody wherein said label comprises a radioactive tracer, an enzyme or a fluorescent or chemiluminescent label, detecting any sandwich formed by said antibodies or fragments with said neurogranin, wherein any enhanced presence of said sandwich in the CSF of the test subject as compared to normal subjects indicates an increased probability of brain damage in the test subject.

2. The method of claim 1, wherein the subject is human.

* * * * *